United States Patent [19]
Ryan et al.

[11] Patent Number: 5,871,471
[45] Date of Patent: Feb. 16, 1999

[54] DISPOSABLE VALUE ASSEMBLY FOR REUSABLE SURGICAL TROCAR

[75] Inventors: Dana Wm. Ryan, Davie; Joel F. Giurtino, Miami; Thomas O. Bales, Coral Gables, all of Fla.

[73] Assignee: Symbiosis Corporation, Miami, Fla.

[21] Appl. No.: 458,135

[22] Filed: Jun. 2, 1995

Related U.S. Application Data

[62] Division of Ser. No. 91,237, Jul. 13, 1993, Pat. No. 5,549,565.

[51] Int. Cl.⁶ .................................................. A61M 5/178
[52] U.S. Cl. ........................ 604/167; 604/169; 604/256; 137/849
[58] Field of Search ................................ 604/164, 165, 604/167, 169, 246, 247, 256, 905; 137/843, 845, 849; 251/149.1

[56] References Cited

U.S. PATENT DOCUMENTS

| | | | |
|---|---|---|---|
| 4,430,081 | 2/1984 | Timmermans | 604/256 |
| 4,946,133 | 8/1990 | Johnson et al. | 251/149.1 |
| 5,423,761 | 6/1995 | Hein et al. | 604/167 |

*Primary Examiner*—Corrine M. McDermott
*Attorney, Agent, or Firm*—David P. Gordon

[57] ABSTRACT

A surgical trocar assembly includes a disposable valve assembly, a cannula assembly, and a trocar with a handle. The cannula assembly includes a cannula base having a valve assembly coupling device at its proximal end, and a cannula extending from its distal end. The disposable valve assembly has a coupling device for removably coupling it with the cannula base. The valve assembly also includes a valve body with a fluid passage communicating with the hollow cannula when it is coupled to the cannula base. A slit or flapper valve and a universal washer are mounted within the valve body and allow the insertion of the trocar or other endoscopic instruments therethrough while providing a fluid sealing of the fluid passage. The valve assembly may be provided with a side port which optionally contains an automatic valve actuated by a luer coupling. Several different valve assembly-cannula base couplings are disclosed as well as several different types of trocars.

24 Claims, 19 Drawing Sheets

FIG. 2i
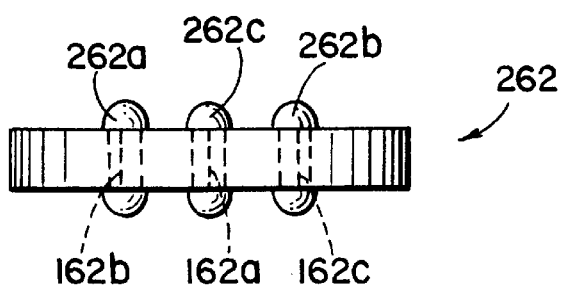
FIG. 2j
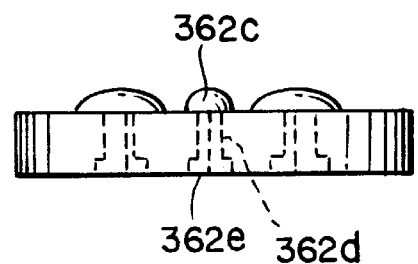
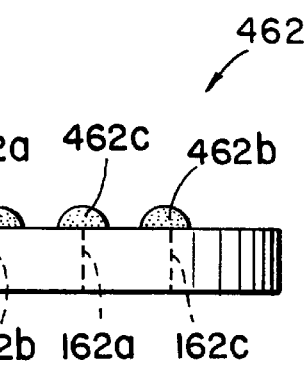
FIG. 2k
FIG. 2l
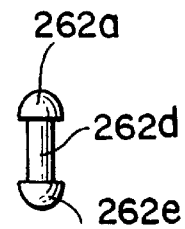
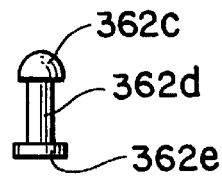
FIG. 2m
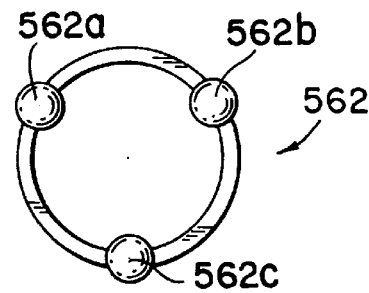
FIG. 2n

FIG. 11a
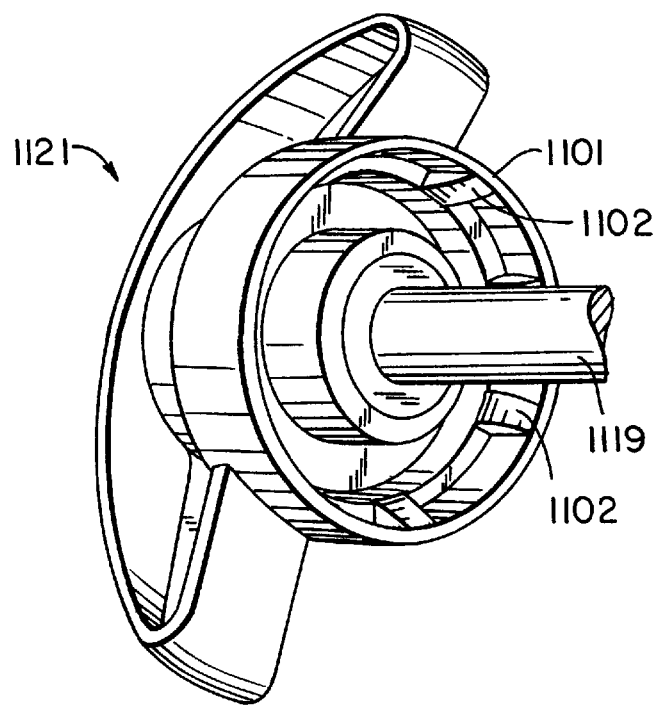
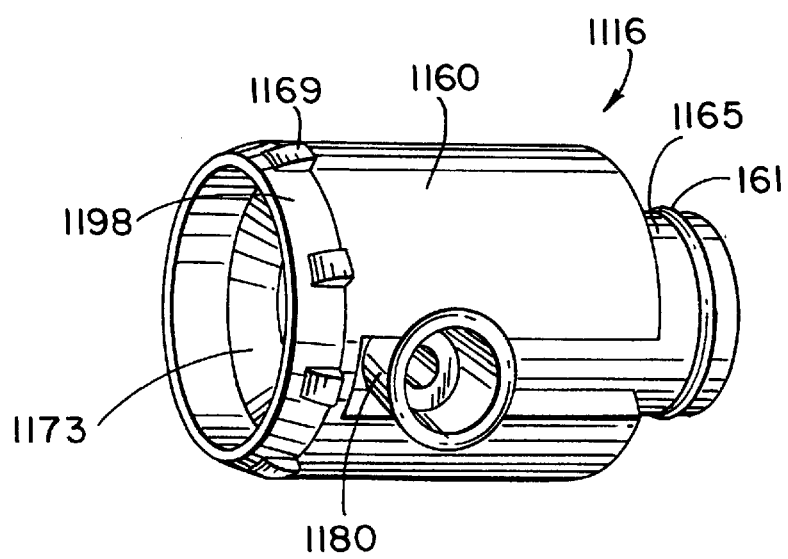
FIG. 11b

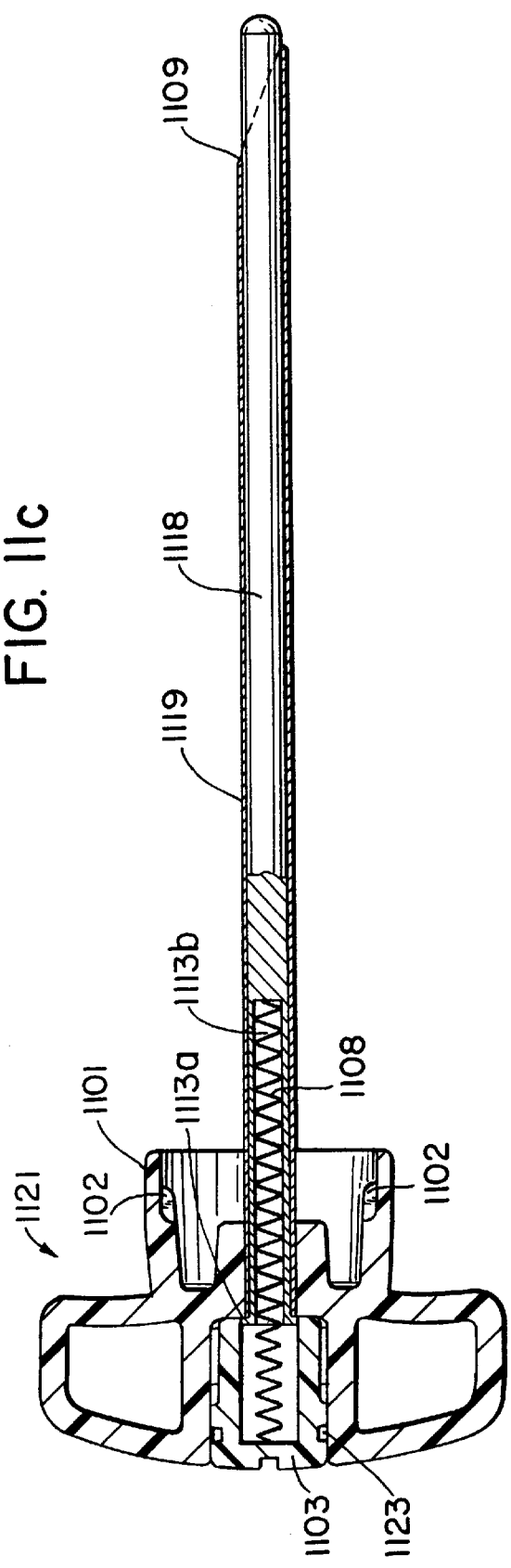
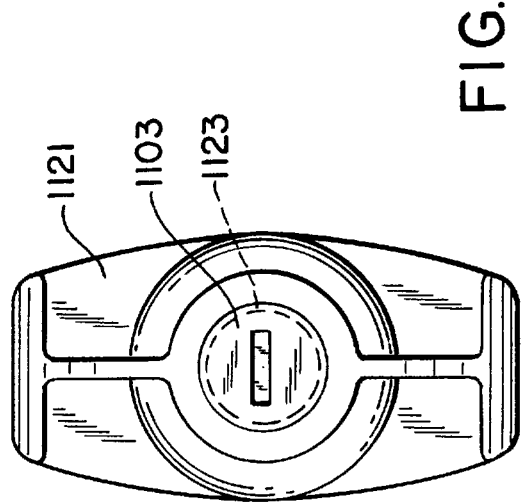

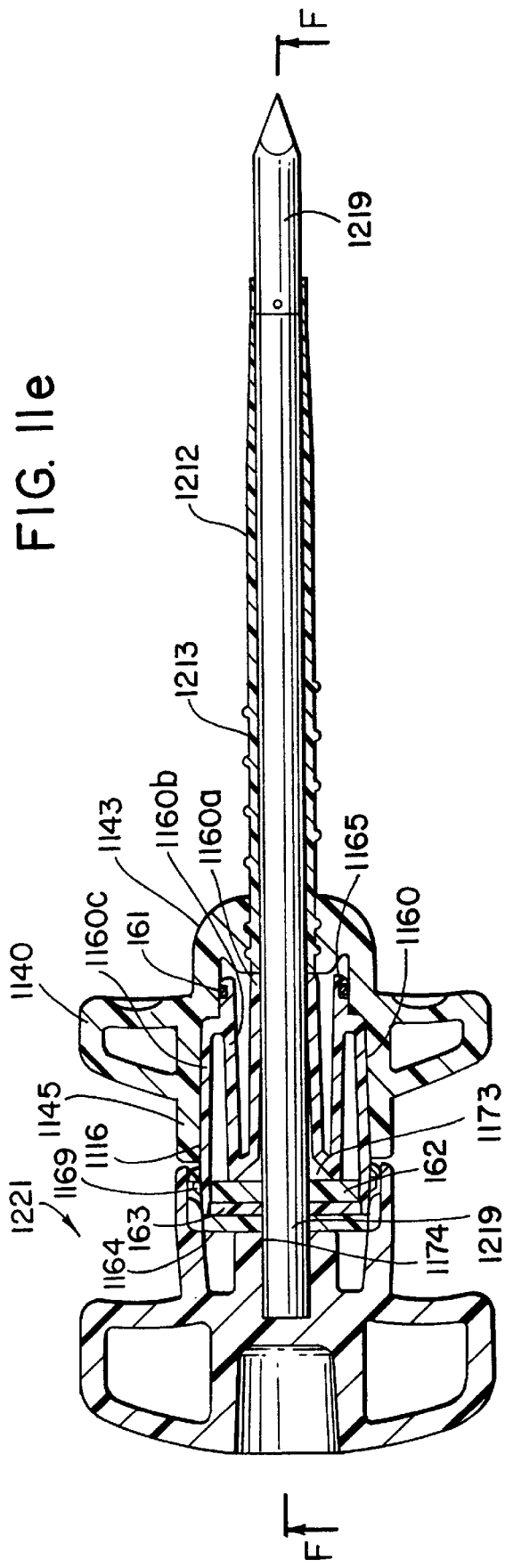
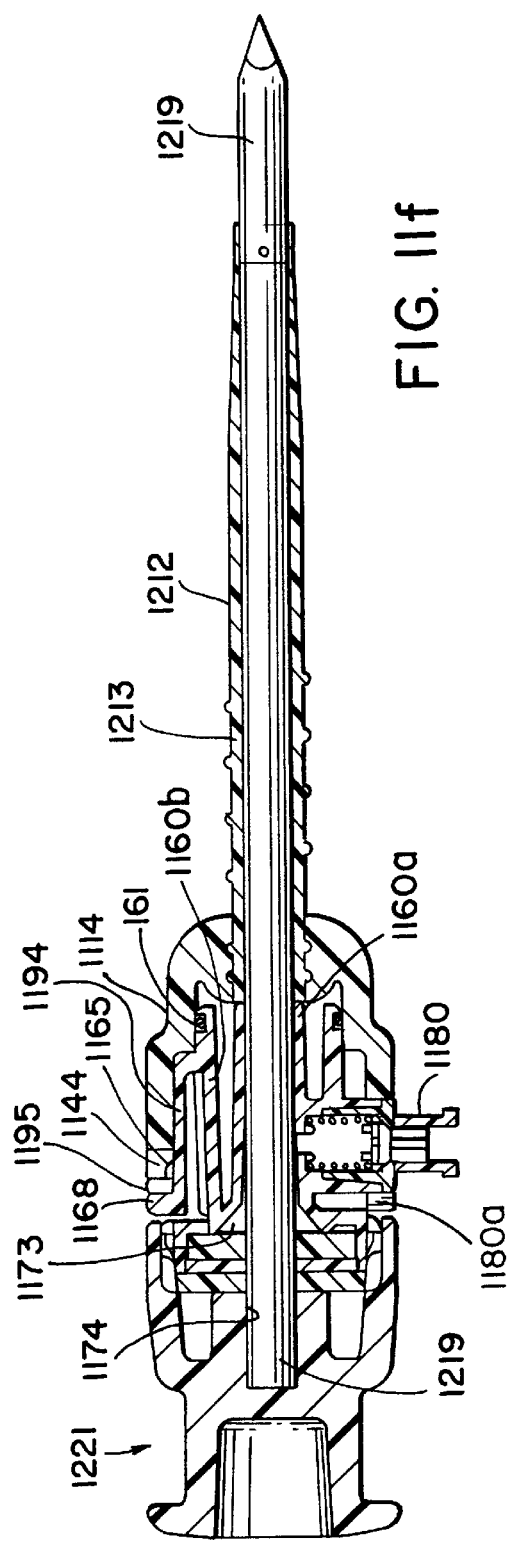
FIG. 11e
FIG. 11f

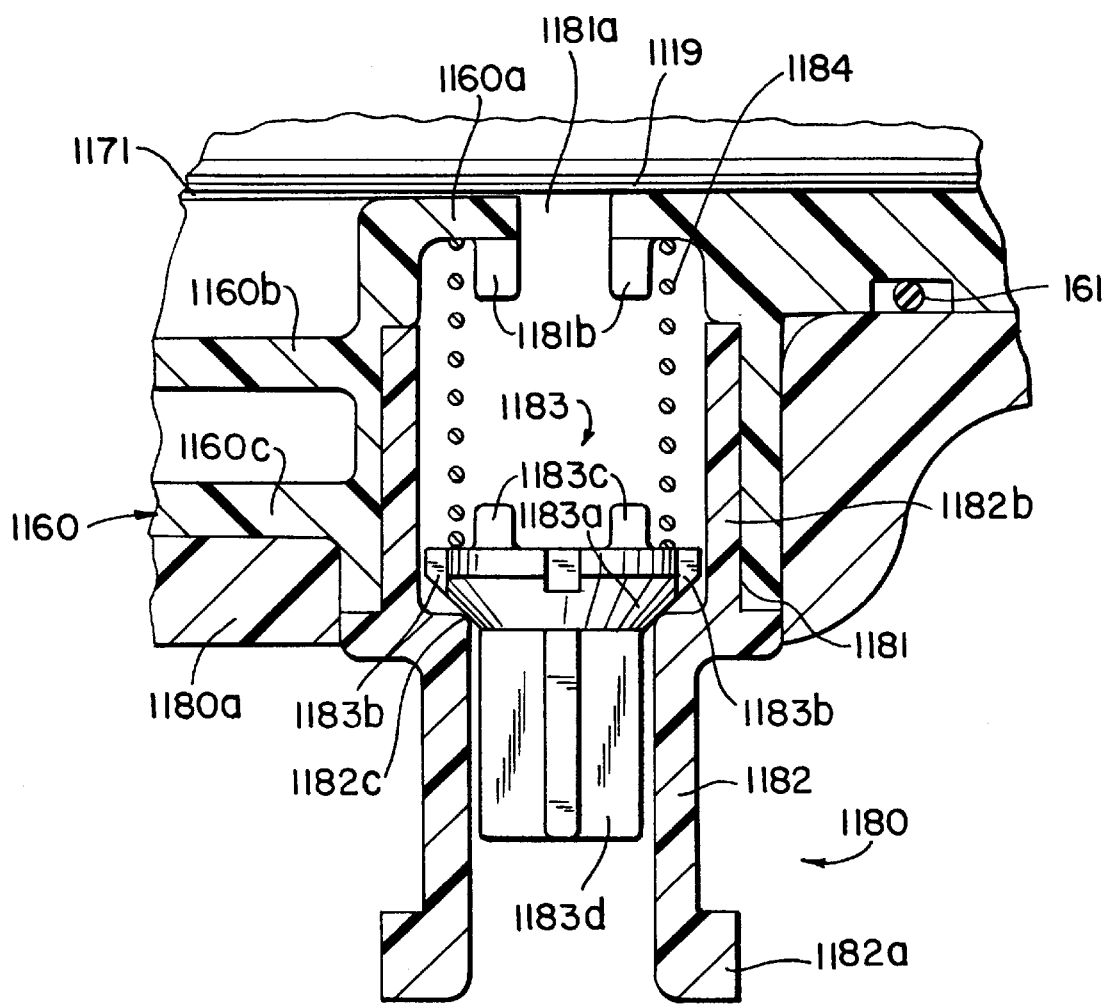

DISPOSABLE VALUE ASSEMBLY FOR REUSABLE SURGICAL TROCAR

This application is a divisional application of Ser. No. 08/091,237, filed Jul. 13, 1993, now U.S. Pat. No. 5,549,565.

BACKGROUND OF THE INVENTION

1. Field of the Invention

This invention relates to surgical trocars. More particularly, this invention relates to a reusable trocar and trocar tube having a removable disposable valve assembly.

2. State of the Art

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. Various surgical viewing telescopes, cameras, lenses, or other viewing instrumentation are inserted through one or more trocar tubes, while a cutter, dissector, or other surgical instrument is inserted through another trocar tube for the purpose of manipulating and/or cutting the internal organ or tissue. Sometimes it is desirable to have several trocar tubes in place at once in order to receive several surgical instruments. In this manner, organs or tissue may be grasped with one surgical instrument, and simultaneously may be cut with another surgical instrument; all under view of the surgeon via the viewing instrumentation in place.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year.

Several advances have been made in the art of trocars and trocar tubes. In general, a trocar (stylet) is inserted into a trocar tube (cannula) so that the distal end of the solid trocar extends beyond the distal end of the hollow trocar tube. The trocar and trocar tube are inserted together into the patient's body and the trocar is then removed from the trocar tube leaving the trocar tube in the patient's body to act as a pathway for the subsequent insertion of endoscopic tools. Trocar tubes are also used for insufflation and desufflation of certain fluids such as the insufflation of $CO_2$ under pressure during various endoscopic procedures. In these applications, trocars must be fitted with some type of sealing mechanism to prevent the leakage of gasses. U.S. Pat. No. 3,994,287 to Turp et al. discloses a disposable plastic trocar tube having a flange portion containing a sealing valve assembly. The valve assembly consists of an elastic ring with an axial opening of reduced diameter. The elastic ring acts as a sealing gasket between the endoscopic tool and the proximal opening of the trocar.

While the introduction of sealing valve means in trocars has definite advantages, disassembly of the valves for cleaning, and the subsequent reassembly and sterilization of these valves is often difficult and time consuming. This is particularly so with more sophisticated valves such as the ball valve disclosed in U.S. Pat. No. 4,379,458 to Bauer et al. As a result of the difficulties in cleaning the valves of the reusable trocars, a large disposable trocar market has emerged. The use of disposable trocars, however, is costly both in actual per operation equipment costs, as well as in the disposal of the medical waste.

Other improvements in trocar assemblies include various safety systems which sometimes interact with sealing valve mechanisms to prevent accidental punctures by the sharp distal end of the trocar. U.S. Pat. No. 4,654,030 to Moll et al. discloses a trocar having a coaxial spring loaded safety shield which extends over the distal sharp point of the trocar. A trocar tube having an elastomeric gasket and a flapper valve interacts with the safety shield so that the sharp point of the trocar can only be exposed when the flapper valve is opened. Similar arrangements are disclosed in U.S. Pat. No. 4,931,042 to Holmes et al. and U.S. Pat. No. 5,032,206 to Lander.

Other innovations in trocar tubes include the addition of helical threads on the surface of the trocar tube, as shown in U.S. Pat. No. 5,009,643 to Reich et al., in order to better hold the trocar tube in place in the patient.

Perhaps the most commonly used trocar assembly today is the safety trocar with flapper valve assembly similar to those described by Moll et al., Holmes et al., and Lander. Some of the improvements to these types of trocars include an improved valve seat and plug for the flapper valve to assure a gas-tight seal when the flapper valve is closed as is described in U.S. Pat. No. 5,053,016 to Lander. It is, however, a continuing disadvantage of trocar tubes having sealing valves that they are either difficult to disassemble, sterilize, and reassemble, or alternatively that they are intended for disposal after a single use. These disposable trocar tubes are relatively expensive and, as mentioned above, endoscopic surgical procedures often require several trocar tubes to be in use simultaneously.

SUMMARY OF THE INVENTION

It is therefore an object of the invention to provide a reusable surgical trocar and tube with a removable disposable sealing valve portion.

It is also an object of the invention to provide a surgical trocar tube with a sealing valve portion that is easily removed and replaced.

It is another object of the invention to provide a surgical trocar tube having a removable sealing valve portion which remains securely attached to the trocar tube when in use.

It is a further object of the invention to provide a number of different types of sealing valve portions which are usable with a reusable trocar tube to suit particular requirements of different procedures.

It is yet another object of the invention to provide a number of different reusable trocars for use with the disposable valve assembly and reusable trocar tube of the invention, including a safety tip trocar, to suit different requirements of different procedures.

It is still another object of the invention to provide a safety tip trocar which is easily cleaned for reuse.

It is even a further object of the invention to provide a trocar assembly having all of the advantages of the existing disposable trocar assemblies of the art while having the additional advantage of being sterilizable and reusable except for a removable sealing valve assembly.

An additional object of the invention is to provide a low friction slit valve which may be used in a trocar assembly.

Another object of the invention is to provide an automatic insufflation valve which is opened by the coupling of a connection such as a luer mechanism to the insufflation valve, and closed by the uncoupling of the same.

In accord with these objects which will be discussed in detail below, the trocar assembly of the present invention includes three major assemblies: a reusable trocar having a handle; a reusable cannula (trocar tube) having a base; and a removable disposable sealing valve assembly. The sealing valve assembly is removably coupled to the cannula base and the trocar is insertable through the sealing valve assembly into the cannula. Typically, the trocar handle covers at least a portion of the sealing valve assembly when the reusable trocar is fully inserted into the cannula. The trocar is removable from the cannula and sealing valve assembly without uncoupling the sealing valve assembly from the cannula.

The sealing valve assembly preferably includes a body having a receiving well for holding a sealing valve such as a slit or flapper valve and a universal washer combination. A valved side port is optionally provided on the body. An annular snap-on valve cap covers the universal washer and slit or flapper valve when assembled and holds them in place.

The coupling of the valve assembly to the cannula base is accomplished by threaded means, bayonet means, spring biased quick connect means such as a latch, or other such means on the valve assembly and/or on the cannula base. The cannula is preferably a metallic shaft which is insert molded into the cannula base. A metallic cannula sleeve having external threads for anchoring to fascia and an optional cannula seal ring are provided on a portion of the cannula close to the cannula base. The preferred cannula base includes a wide receiving mouth for holding the valve assembly and a somewhat narrower throat leading to the cannula. The wide receiving mouth is preferably provided with side openings to accommodate the side port of the valve assembly and for removably coupling the valve assembly to the cannula base. The valve assembly preferably has a relatively wide body which fits snugly inside the wide mouth of the cannula base and a relatively narrow distal end with a fluid sealing means such as an O-ring or other sealing mechanism for sealing with the throat of the cannula base.

A number of different trocars are provided for use with the trocar assembly of the invention, including a blunt tip, a sharp pyramid tip, and a spring-loaded safety tip. According to one embodiment, the tips may be interchangably screwed into the distal end of a trocar rod. According to a preferred safety tip trocar embodiment, a spring biased blunt tipped rod is provided which extends within and beyond a sharp tip. A spring which biases the rod is housed in the trocar handle and the spring and rod are easily removable from the trocar through a screw cap in the top of the handle. In this manner, after use, the components may be disassembled, cleaned, reassembled, and autoclaved prior to reuse.

Other aspects of the invention include: providing the side port of the valve assembly as an automatic side port valve which opens only when a male luer fitting is inserted into side port; providing improved proximal automatic valve means such as a tricuspid slit valve with contact bumps or rails in order to reduce friction between the disposable valve assembly and trocars or other instruments inserted through the valve assembly; and providing anti-rotational mating splines or grooves on two or all three of the valve assembly, the trocar assembly, and the cannula assembly so as to prevent rotation of the assemblies relative to each other.

Additional objects and advantages of the invention will become apparent to those skilled in the art upon reference to the detailed description taken in conjunction with the provided figures.

BRIEF DESCRIPTION OF THE DRAWINGS

FIG. 1a is a cross section along the line A—A in FIG. 1;

FIG. 2i is a side elevation view of the tricuspid valve of FIG. 2g;

FIG. 2j is a side elevation view of the tricuspid valve of FIG. 2h;

FIG. 2k is a view similar to FIGS. 2i and 2j but of a further alternate embodiment of the tricuspid valve;

FIG. 2l is a side elevation view of bump insert used in the valve of FIGS. 2g and 2i;

FIG. 2m is a side elevation view of a bump insert used in the valve of FIGS. 2h and 2j;

FIG. 2n is a top plan view of an alternate embodiment of a bump insert;

FIG. 11a is a perspective view of the trocar handle for use with the valve assembly and cannula base of FIG. 11;

FIG. 11b is a perspective view of the valve body of FIG. 11;

FIG. 11c is a longitudinal cross sectional view of the safety trocar for use with the arrangement of FIG. 11;

FIG. 11d is a top view of the trocar of FIG. 11c;

FIG. 11e is a cross-sectional view the apparatus of FIGS. 11 and 11a assembled as a non-safety sharp tipped trocar;

FIG. 11f is a cross section through line F—F of FIG. 11e;

FIGS. 12a and 12b are side views in partial cross section of a preferred valve means for use with the invention shown respectively in closed and open positions.

DETAILED DESCRIPTION OF THE PREFERRED EMBODIMENTS

Figure 1:
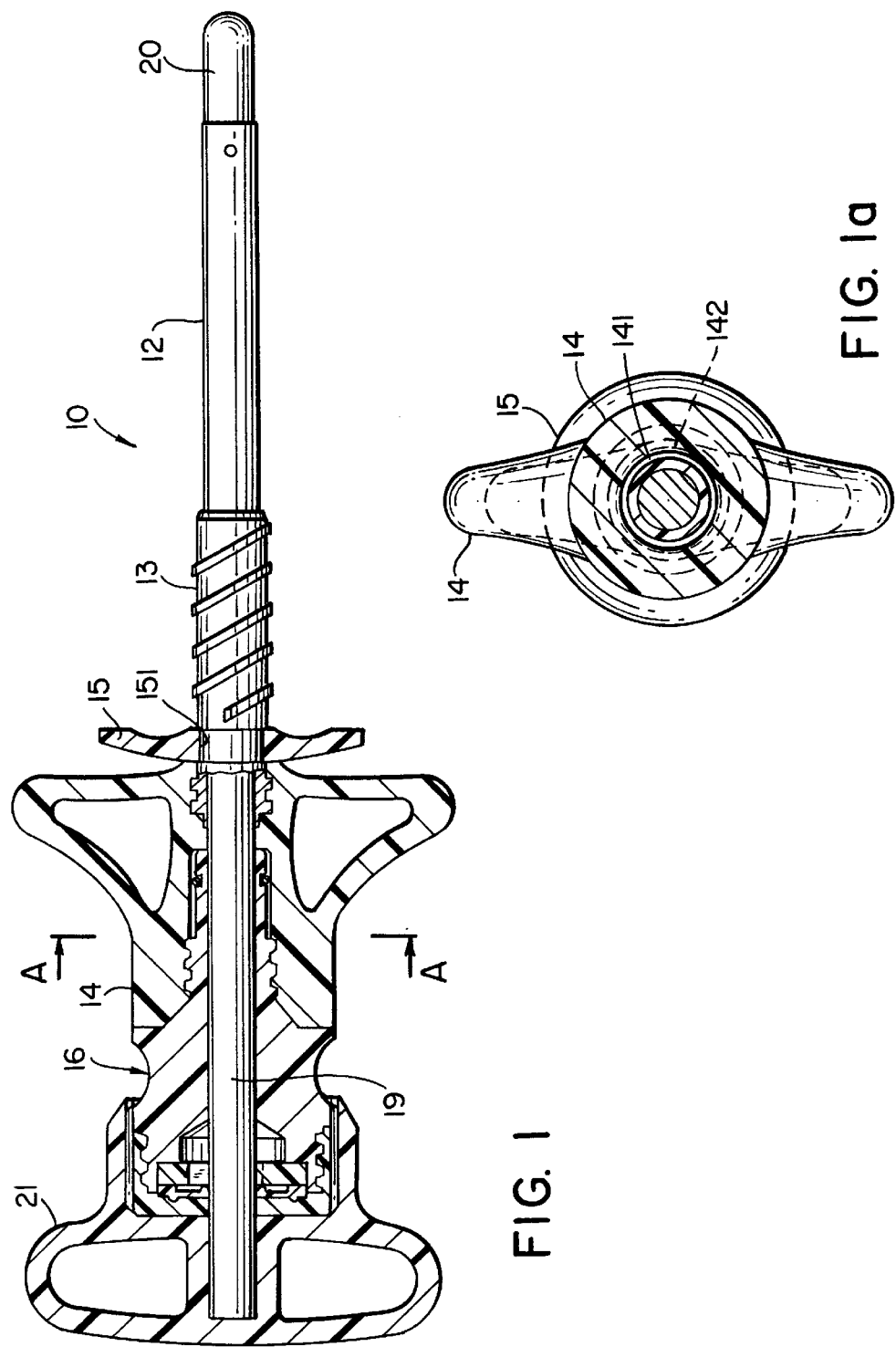
FIG. 1 is a side view in partial cross section of a first embodiment of the invention.
Figure 2:
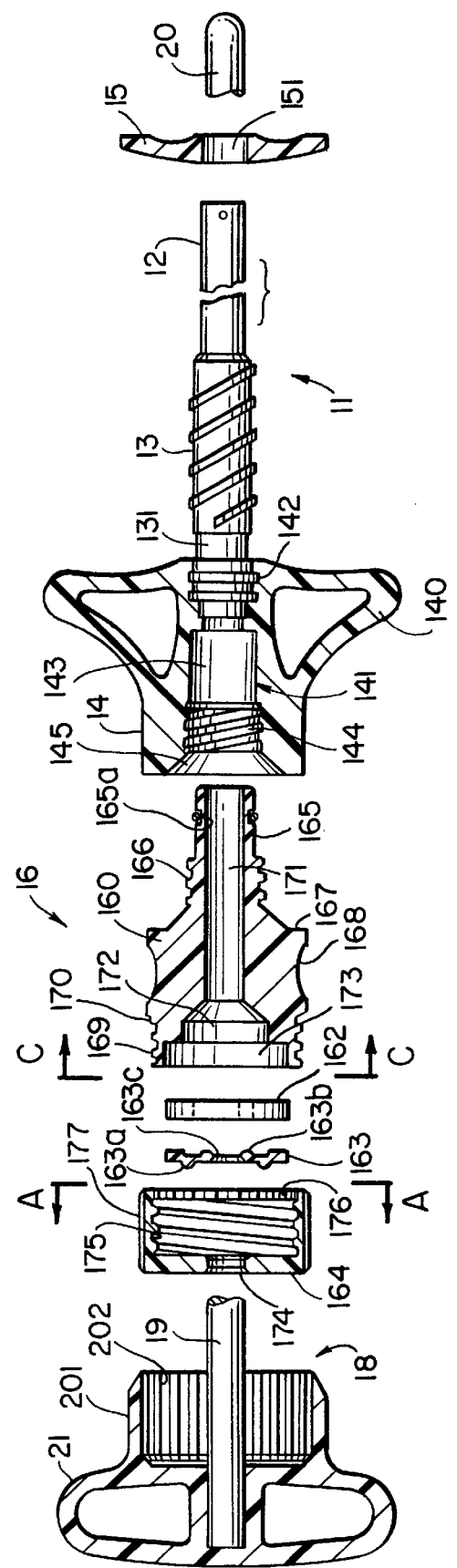
FIG. 2 is an exploded view of the embodiment of FIG. 1.

Referring now to FIGS. 1, 1a and 2, the trocar assembly 10 of the present invention generally includes a hollow trocar tube or cannula assembly 11 having a cannula 12 insert molded in a cannula base 14, a sealing valve assembly 16 removably coupled to the cannula base 14, and a trocar assembly 18 having a trocar 19 with a distal tip 20 and a proximal handle 21 which is removably inserted through the valve assembly 16 and the cannula 12.

The cannula 12 of the cannula assembly 11 is preferably provided with a threaded cannula sleeve 13 and an optional external groove 131 for receiving an optional seal ring 15 which is mounted on a proximal end of the cannula adjacent the cannula base 14 as seen in FIG. 1. The seal ring 15 is advantageous in forming a seal on the surface (skin) of a patient and preventing leakage of gases and body fluids from the incision site. If desired, the cannula 12 and threaded cannula sleeve 13 can be formed as a single integral part.

According to a first embodiment of the invention, the cannula base 14 is preferably provided with one or more external flanges 140 for gripping. Internal the cannula base 14, a passageway 141 is provided. Passageway 141 includes distal opening 142 in which the cannula 12 is held, a cylindrical passage 143, a threaded portion 144, and a tapered portion 145. As will be discussed in more detail hereinafter, the cylindrical 143, threaded 144, and tapered 145 portions of passage 141 are used to receive and couple to the valve assembly 16. It will be appreciated that the cannula 12 and cannula base 14 are preferably formed in a manner such that they are easily cleaned (by autoclaving or other sterilization techniques) and are intended to be reusable.

The valve assembly 16 of the embodiment of FIGS. 1 and 2 includes a valve body 160, a sealing mechanism such as an O-ring 161, a slit (e.g., tricuspid) valve 162, a universal washer 163, and a cap 164. The external surface of the valve body 160 includes a distal cylindrical extension 165. The cylindrical extension 165 may either be formed with a molded sealing protrusion which acts as a sealing mechanism, or with a distal groove 165a which receives the sealing O-ring 161. The external surface of the valve body 160 also includes a first threaded section 166 which mates with threads 144 of the cannula passageway, a tapered surface 167 which increases in diameter as it extends from the distal end to the proximal end and which mates with tapered surface 145 of the cannula passageway, bowed finger indentations 168, a proximal second threaded section 169, and ratchet teeth 170 between the threaded section 169 and the finger indentations 168.

Figure 2A:
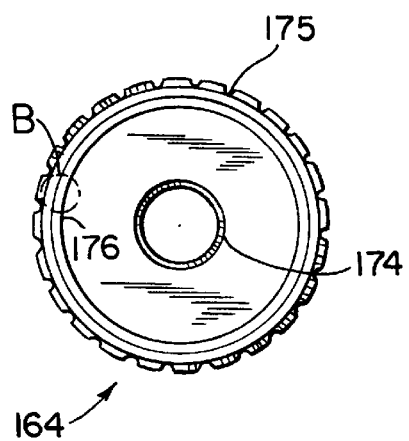
FIG. 2a is a sectional view along line A—A in FIG. 2.
Figure 2C:
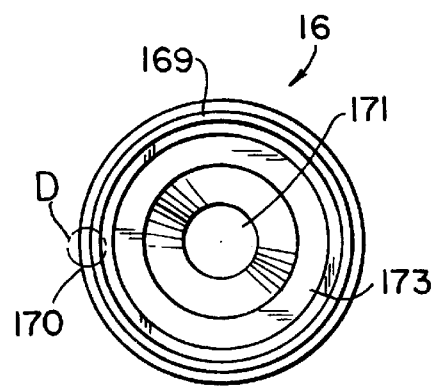
FIG. 2c is a sectional view along line C—C of FIG. 2.
Figure 2B:
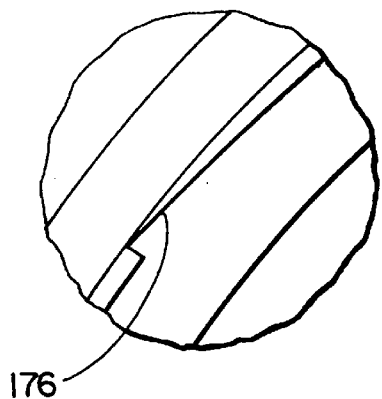
FIG. 2b is an enlarged detail of a portion of FIG. 2a identified by the circle B.
Figure 2D:
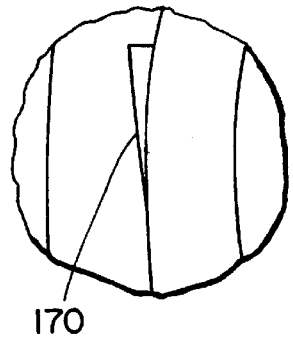
FIG. 2d is an enlarged detail of a portion of FIG. 2c identified by the circle D.

Comparing FIGS. 1 and 2, it will be appreciated that the valve body 16 is provided with an internal throughbore 171 which communicates with the cannula 12 when the valve body 160 is coupled to the cannula base 14. Throughbore 171 widens at 172 at its proximal end, and extends into a well 173 which receives the slit valve 162 and the universal washer 163. These are held in place by a covering cap 164 which engages threads 169 surrounding the proximal end of the valve body 16. As shown in FIGS. 2 and 2a, the covering cap 164 includes a central through bore 174, internal threads 175, an internal ratchet locking surface 176, and external splines 177. It will be appreciated that after the slit valve 162 and the universal washer 163 are placed in the well 173 of the valve body 16, the covering cap 164 is placed over the threads 169 of the valve body 16 and turned until internal threads 175 of the cap engage the threads 169 of the body and the pieces are brought snugly together. The central throughbore 174 in the covering cap 164 provides a passage for the trocar 19 through the universal washer 163 and the slit valve 162, into the internal through bore 171 of the valve body 16 and thus into the cannula 12 as shown in FIG. 1.

It is contemplated by the present invention that once assembled, the valve body 160, slit valve 162, universal washer 163 and covering cap 164 will not be disassembled and that the entire valve assembly will be removed from the cannula base 14 after use for disposal. With this in mind, the valve body 160 and the covering cap 164 are provided with a ratchet-like locking means 170, 176 respectively. FIGS. 2a–2d show these in greater detail. Referring now to FIGS. 2a–2d, it will be seen that the internal lip of the covering cap 164 is provided with a plurality of ramped ratchet teeth 176 and the distal part of the proximal threaded portion 169 of the valve body 160 is provided with a plurality of oppositely ramped ratchet teeth 170. Those skilled in the art will appreciate that when the covering cap 164 is screwed tightly onto the valve body 160, these respective ramped teeth (176 and 170) engage each other to allow a screw coupling of the pieces while preventing an uncoupling rotation of the pieces.

Those skilled in the art will appreciate that the completed valve assembly 16 may be coupled to the cannula base 14 by holding the valve body 160 at its bowed finger indentations 168, inserting the cylindrical extension 165 of the valve body 160 into the cylindrical passage 143 of the cannula base 14, and turning the valve body 160 so that the distal threads 166 engage the threads 144 of the cannula base and the two pieces are brought snugly together as shown in FIG. 1. When that happens, O-ring 161 seats inside the cylindrical passage 143 of the cannula base 14 and provides a fluid-tight coupling of the throughbore 171 with the cannula 12. Likewise, the completed valve assembly 16 may be removed from the cannula base 14 by gripping the valve body at finger indentations 168 and rotating in the opposite direction until the valve body is uncoupled from the cannula base 14.

As mentioned briefly above, the covering cap 164 of the valve assembly 16 is provided with external surface splines 175. These are provided for engagement with internal splines 202 of the distally extending sleeve portion 201 of the trocar handle 21. As seen best in FIG. 1, when the reusable trocar 18 is inserted through the throughbore 174 in the valve covering cap 164, and through the washer 163, slit valve 162, throughbore 171 in the valve body 160, and the cannula 12, the internal splines 202 in the trocar handle 21 engage the external splines 175 on the covering cap 164 of the valve body 160 as the trocar tip 20 extends past the distal end of the cannula 12. These splines prevent the trocar handle from rotation relative to the valve body 14 (compare FIG. 8 described below). During insertion, flaps of the slit valve 162 are pushed into the widening 172 of throughbore 171. Also, during insertion, the washer 163 (and to a lesser extent, the slit valve 162) seals around the trocar 19 and prevent fluids or gases which might work their way up the trocar assembly in an annulus between the trocar 19 and the inner wall of the cannula and valve assembly from escaping. Upon withdrawing the trocar 19 from the cannula 12 and valve assembly 16, the slit valve 162 closes automatically and prevents the escape of gas or fluids.

The trocar handle 21 and cannula base 14 are both preferably molded from a steam autoclavable plastic or polymer such as "UDEL Polysulfone" or its equivalent, although all or parts of one or the other can be made of metal. The valve body 160 and covering cap 164 are each preferably formed from an injection molding of plastic such as polypropylene, polycarbonate or their equivalents. The trocar 19 is preferably formed from stainless steel and is preferably insert molded into the handle 21. Likewise, the cannula 12 with integral sleeve 13 is preferably formed from stainless steel which is insert molded into the cannula base 14. The cannula sealing ring 15, the slit valve 162, and the universal washer 163 are each preferably molded from medical grade silicone. The cannula sealing ring 15, therefore, has enough elasticity to be stretched over the cannula sleeve 13 so that its central hole 151 embraces groove 131 in the cannula sleeve 13. The slit valve 162 and universal washer 163 have sufficient elasticity to allow passage of trocar 19 while effectively sealing the valve body from entry or exit of fluids.

Figure 2E:
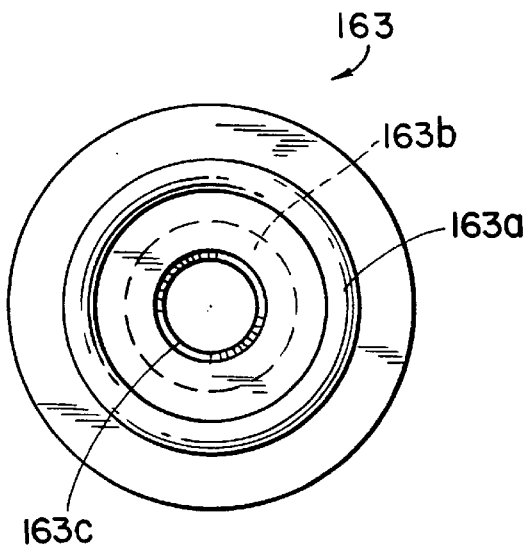
FIG. 2e is an enlarged plan view of the universal washer.

FIG. 2e shows an enlarged plan view of the universal washer 163. The universal washer 163 is provided with a pair of annular rings 163a, 163b on opposite sides of central opening 163c. These annular rings add flexibility to the washer so that little resistance is offered when inserting and removing the trocar.

Figure 2F:
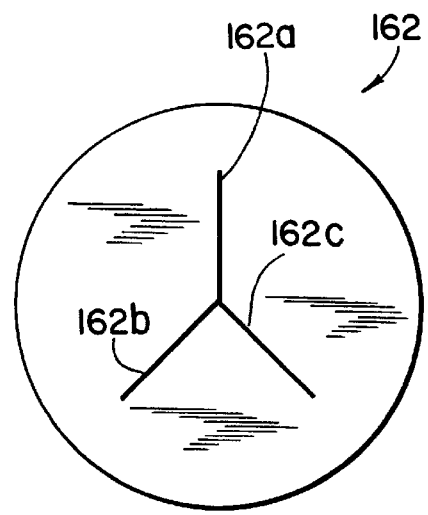
FIG. 2f is an enlarged plan view of the tricuspid valve.
Figure 2G:
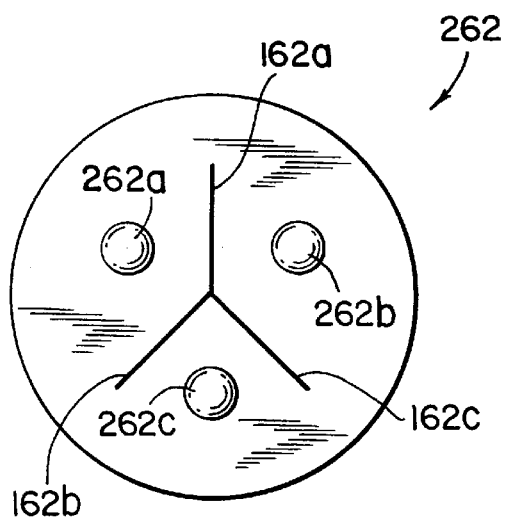
FIG. 2g is a view similar to FIG. 2f but of an alternate embodiment of the tricuspid valve.
Figure 2H:
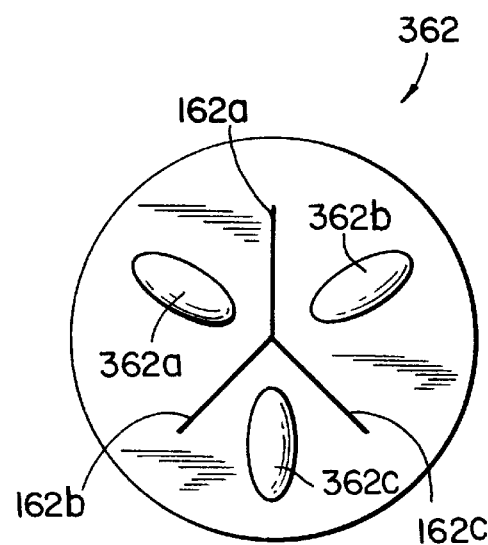
FIG. 2h is a view similar to FIG. 2f but of a further alternate embodiment of the tricuspid valve.

FIG. 2f shows an enlarged plan view of the tricuspid valve 162. The tricuspid valve is typically constructed of a silicone disk with three slits 162a, 162b, 162c converging at the center of the disk. When a trocar is inserted into the valve, portions of the valve between the slits are pushed apart. The silicone material offers resistance, however, and this impedes insertion and removal of the trocar. While lubricity could be added to the silicone valve by forming the silicone with a lubricant, or by adding lubricant to the outer surface of the valve, in accord with a preferred aspect of the invention, lubricity is added to the tricuspid valve by providing bumps or buttons made out of polyethylene, polypropylene, TEFLON (a trademark of E. I. DuPont de Nemours of Del.), or equivalents thereof which preferably extend through the valve. FIGS. 2g and 2h show alternate configurations of a tricuspid valve 262 and 362. The bumps 262a–262c or 362a–362c are placed on the surface of the silicone disk in the areas between the slits. The bumps may be glued or snap fit through holes in the disk. They may be almost any shape, but an elongated shape which extends radially away from the center of the disk such as shown in FIG. 2h is preferred. When the trocar or other surgical instrument is inserted through the valve, and the portions of the valve between the slits is spread, the bumps rest against the surface of the trocar or other instrument and provide a slippery surface contact so that the trocar or other instrument is easily inserted and removed.

Figure 2O:
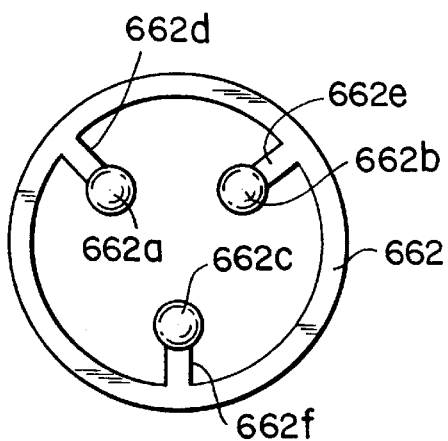
FIG. 2o is a view similar to FIG. 2n but of a further alternate embodiment of a bump insert.

As shown in FIGS. 2i and 2l, the bumps may formed from barbell-like inserts having an upper bump 262a, a middle stem 262d and a lower bump 262e. As mentioned above, the upper and lower bumps may be hemispherical or hemi-elliptoid. The barbell-like pieces are insert molded into the silicone disk. Since in practice, it is only necessary to provide bumps on the proximal side of the disk, the bumps shown on the distal side of the disk in FIG. 2i are for anchoring purposes and do not affect the frictional relationship of the valve and the trocar or other surgical instrument extending through the valve. In this regard, it will be appreciated that the bump-forming inserts may take many forms such as, for example, as shown in FIGS. 2j, 2m, 2n, and 2o. In FIGS. 2j and 2m, the inserts are formed with an upper bump 362c, a middle stem 362d, and a lower flange 362e which aids in anchoring the bumps when they are insert molded in the silicone disk. In order to expedite the insert molding process, a plurality bumps may be formed as a single molded piece as shown in FIGS. 2n and 2o. In FIG. 2n, bumps 562a–562c are coupled by respective stems (not shown) to a web 562 which may take the form of a mesh or a ring. The web 562 is insert molded in the silicone disk. When the slits are made in the disk to create the tricuspid valve, the mesh or ring may or may not be cut by the slits since after the disk is molded around the web, the integrity of the ring or mesh is no longer important. It only acts as an anchor for the bumps, and so long as a piece of the ring is attached to the bump, the bump will be securely anchored in the disk. A similar arrangement of ring 662 is shown in FIG. 2o where bumps 662a–662c are attached to radial arms 662d–662f by stems (not shown). The radial arms displace the bumps from the ring so that the ring may be located outside the range of the slits.

Another embodiment of the tricuspid valve 462 is shown in FIG. 2k. In this embodiment, bumps 462a–462c are formed directly on the disk 462 (i.e., integral therewith) by molding the disk in a mold having recesses for the bumps. The bumps are then coated with TEFLON (shown as a shaded portion in FIG. 2k) or another suitable slippery surface material. Alternatively, the entire surface of the disk is coated with TEFLON or an equivalent thereof. When the trocar enters the tricuspid valve, the bumps engage the surface of the trocar reducing the area of frictional engagement between the valve and the trocar. The TEFLON coating on the bumps further reduces friction between the trocar and the valve when inserting and withdrawing the trocar.

Figure 2P:
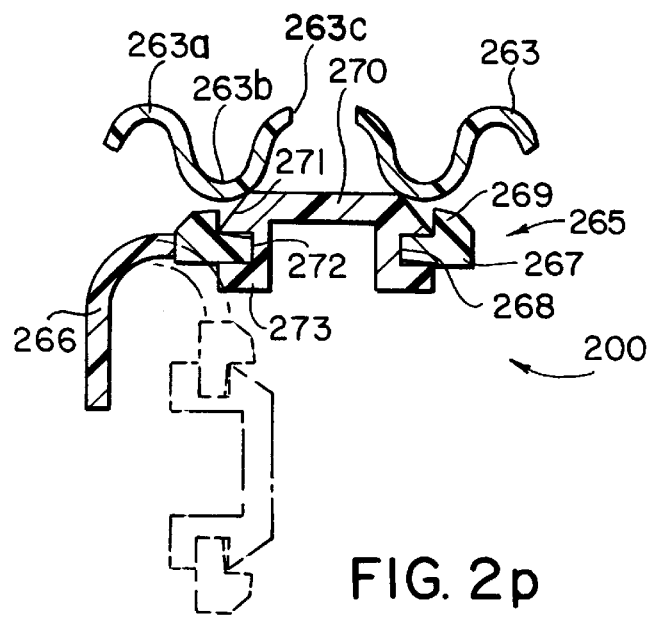
FIG. 2p is a cross sectional view of a flapper valve arrangement according to another embodiment of the invention.

FIG. 2p shows another type of valve arrangement 200 which offers little resistance to the insertion and removal of trocars and surgical instruments. Valve arrangement 200 includes a proximal washer 263 having a central opening 263c and oppositely extending annular bumps 263a, 263b. A distal flapper valve 265 includes a resilient arm 266 coupled to a ring 267 which may be integral therewith. Ring 267 has a central opening 268 and a proximal annular shoulder 269. An insert 270 of polypropylene or its equivalent has a frustoconical proximal end 271, a narrow diameter middle 272 and a flanged distal end 273. Insert 270 is held in the central opening 268 of ring 267 with its frustoconical end 271 resting in shoulder 269, and the flanged end 273 resting against the distal side of opening 268. The resilient arm 266 biases the ring 267 and the insert 270 against the washer 263 as shown in solid lines in FIG. 2p. In this position, the frustroconical end 271 of the insert 270 engages the annular bump 263b of washer 263 and seals the central opening 263c. When a trocar is inserted through the central opening 263c, the flapper valve 265 is moved by the trocar to the position shown in dotted lines (phantom) in FIG. 2p. The slippery insert 270 offers little or no resistance to the trocar or other surgical instrument during insertion and removal. When the trocar or other surgical instrument is removed, the resilient arm 266 biases the valve shut. It will be appreciated by those skilled in the art that universal washer 263 and the flapper valve 265 shown in FIG. 2p are appropriately housed in the valve assembly of the invention.

Figure 2Q:
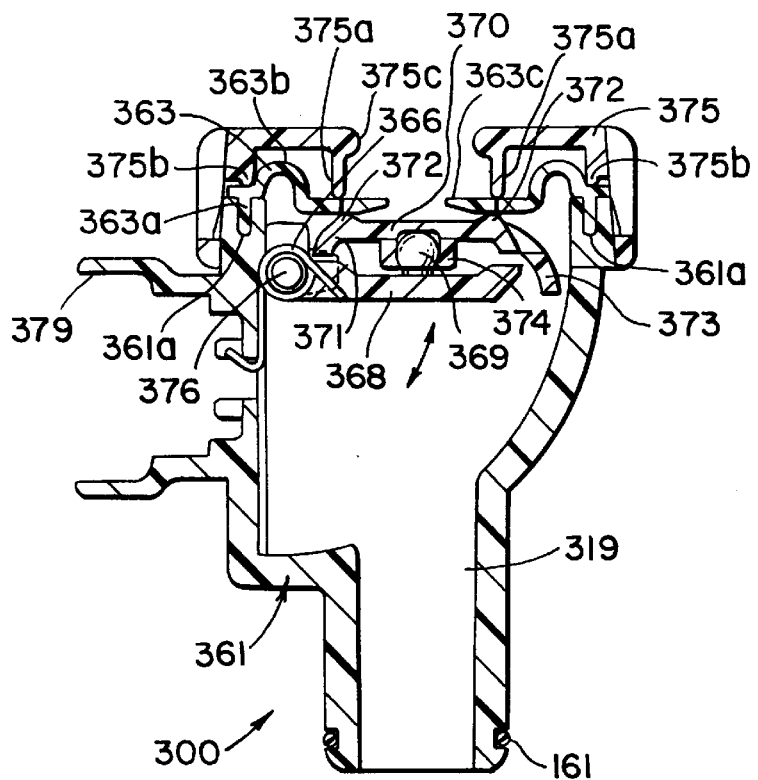
FIG. 2q is a cross sectional view of another embodiment of a flapper valve in a closed position in a valve body having a universal washer.
Figure 2R:
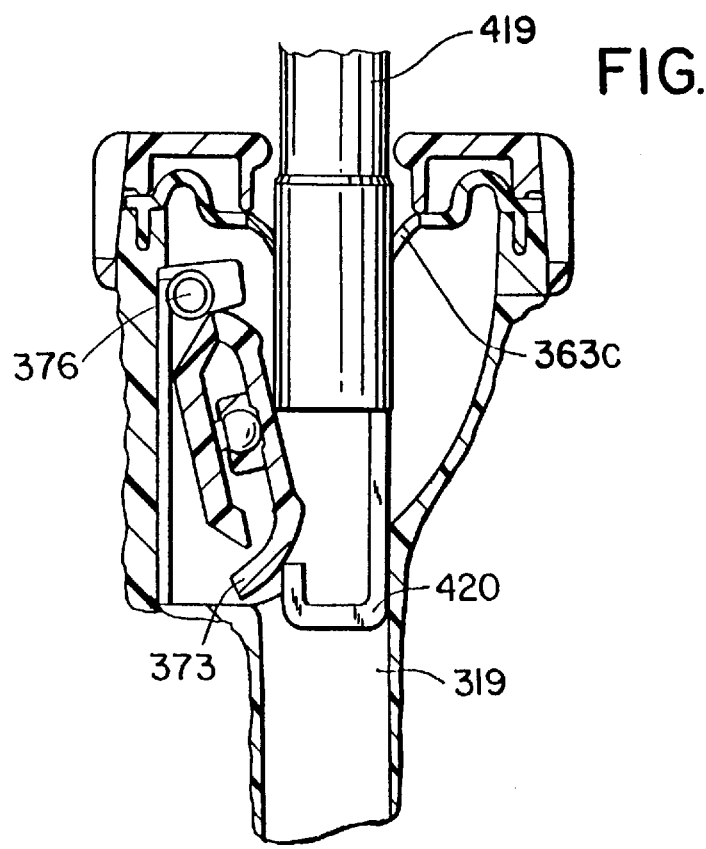
FIG. 2r is a view similar to FIG. 2q showing the flapper valve held in an open position by a J-hook cautery probe.
Figure 2S:
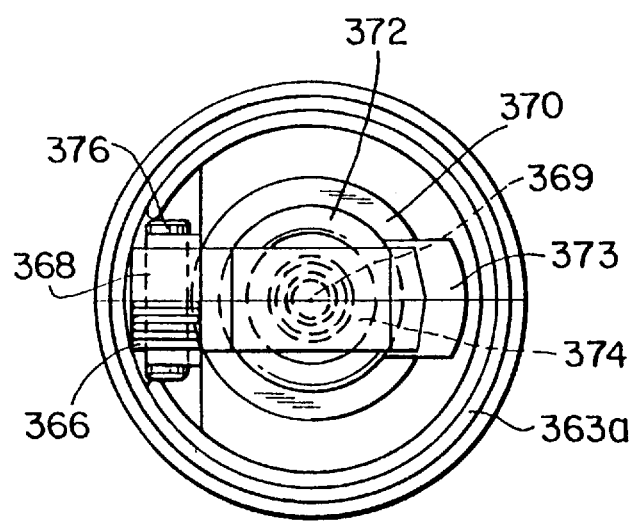
FIG. 2s is a top view of the assembly shown in FIG. 2q.

FIGS. 2q through 2s show a presently preferred embodiment of a valve arrangement 300 in a valve body 361 having a side port 379, a throughbore 319, a proximal valve body cap 375 and a distal O-ring 161. The proximal end of the valve body 361 is provided with a washer receiving annular groove 361a. A universal washer 363 having a central opening 363c, an intermediate annular ripple 363b, and an outer circular flange 363a is placed at the proximal end of the valve body 361 so that the flange 363a engages the groove 361a and the central opening 363c substantially aligns with the throughbore 319 as shown in FIG. 2q. A valve body cap 375 is provided with a central opening 375c, an inner annular flange 375a and an outer annular flange 375b. The annular flanges in the valve body cap engage the universal washer as shown in FIG. 2q. In particular, the outer flange 375b presses the universal washer against the groove 361a in the valve body 361 and the inner flange 375a surrounds the central opening 363c of the washer 363.

The valve body 361 is further provided with a hinge pin 376 adjacent the side port 379. Hinge pin 376 supports a swing arm 368 and a torsion spring 366. Swing arm 368 is provided with a central spherical button 369 which takes the form of ball joint for carrying a sealing cap 370. The sealing cap 370 has a lower central cylindrical socket 374 for receiving the ball 369 (with the ball and socket providing a centering and seal adjusting function), an upper circular lip 372 for engaging washer 363, and a laterally extending downward curved tongue 373. As seen in FIG. 2q, the sealing cap 370 is held by swing arm 368 and is biased against the washer 363 by the torsion spring 366. It will be appreciated that the upper circular lip 372 underlies the inner flange 375a of the valve body cap 375 with the universal washer 363 therebetween. Thus, when the swing arm 368 is biased by the torsion spring 366 to the position shown in FIG. 2q, the upper circular lip 372 of the sealing ring presses against the universal washer 363 (which in turn is limited in its movement by the flange 375a of the valve body cap 375), thereby making a fluid tight seal.

When a surgical probe, such as J-hook cautery probe 419 is inserted into the valve body 361 through the central opening 375c in the valve body cap 375, the distal end 420 of the probe pushes against the sealing cap 370 and moves the swing arm 368 against the bias of spring 366. Concurrently, the edge of the central opening 363c of the universal washer 363 is bent inwards, thereby keeping a fluid seal between the probe 419 and the throughbore 319 of the valve body. The lateral downward extending tongue 373 of the sealing cap 370 assumes the position shown in FIG. 2r and rests against the side of the probe 419 allowing it to be moved in and out of the valve body without entangling the sealing cap. It will be appreciated from FIG. 2r that the length and curvature of the tongue 373 is sufficient to prevent the J-hook end 420 of probe 419 from catching the edge of the sealing cap and pulling it off the swing arm.

Figure 3:
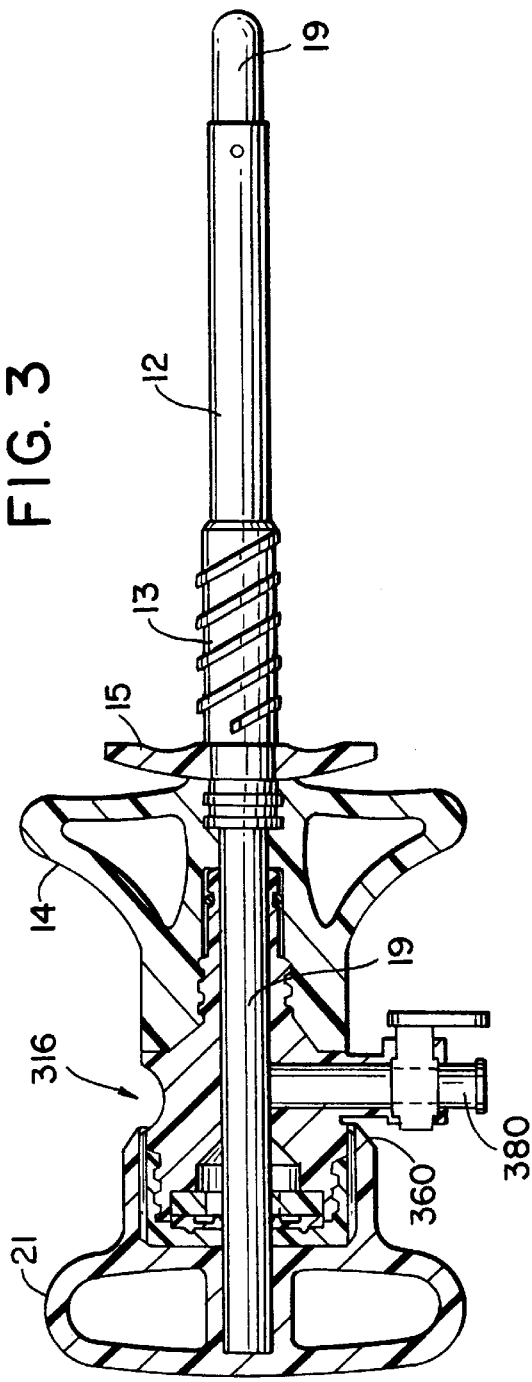
FIG. 3 is a view similar to FIG. 1 showing an embodiment of a valve assembly which includes a side port.

Turning now to FIG. 3, in accord with another embodiment of a valve assembly 316, the valve body 360 is provided with a side port 380 for coupling to a fluid conduit (not shown). In this embodiment of the valve body 360, the side port 380 is seen to include a manual stopcock (compare FIG. 7 described below) and access through side port 380 is manually controlled by the practitioner. Those skilled in the art will appreciate that when the trocar 19 is removed from the valve body 360, fluid flow is permitted between the side port 380 and the cannula 12 if the manual stopcock is in an open position.

Figure 5:
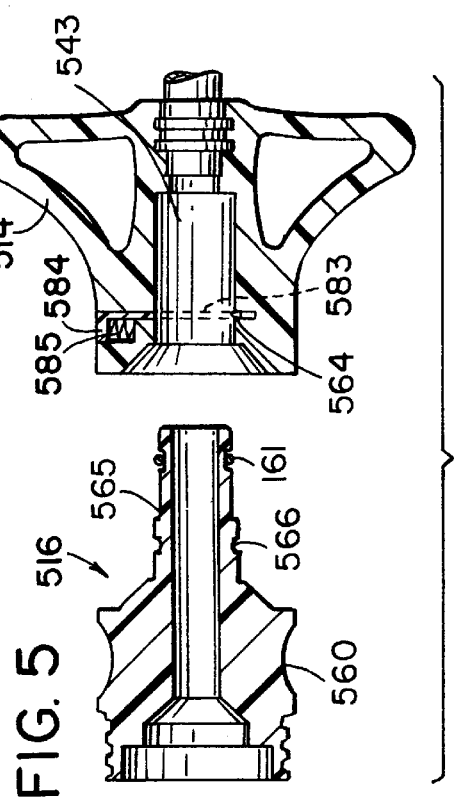
FIG. 5 is a view similar to FIG. 4 showing a third embodiment of the coupling mechanism for the valve assembly and cannula base.
Figure 4:
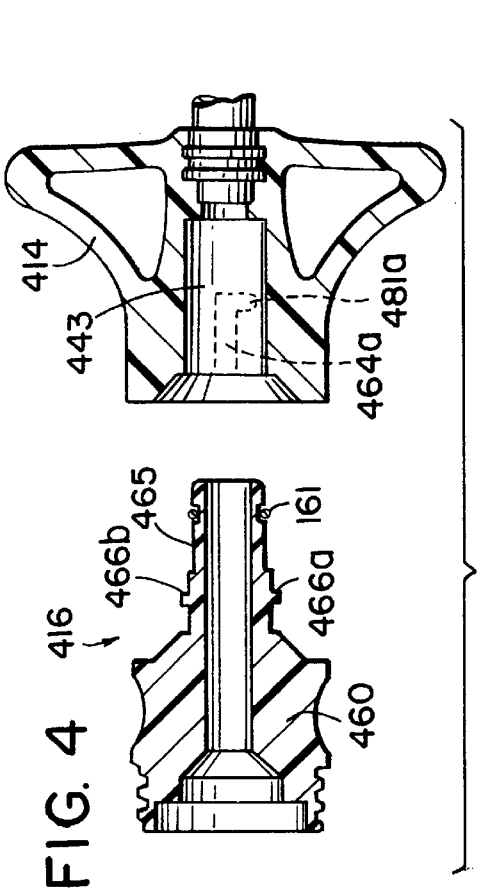
FIG. 4 is a partial exploded view, similar to a portion of FIG. 2, showing a second embodiment of the coupling mechanism for the valve assembly and cannula base.
Figure 6:
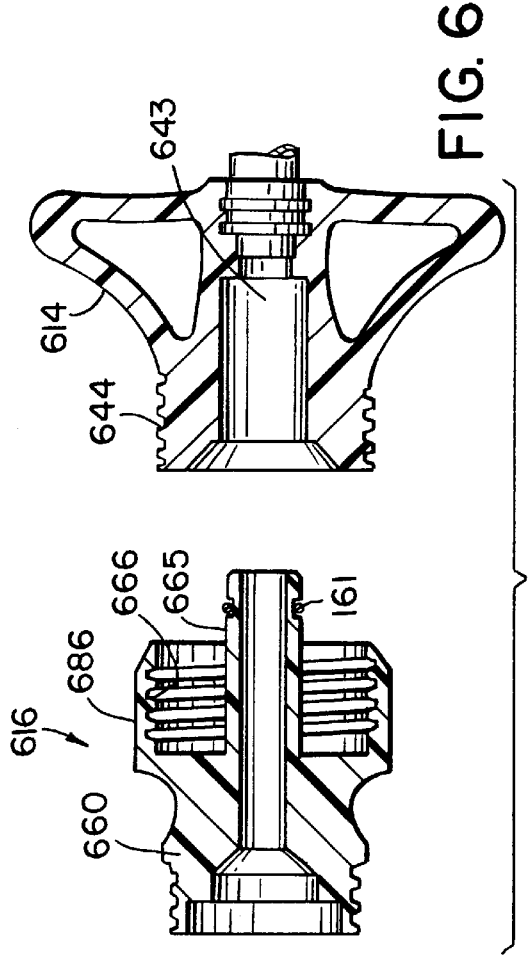
FIG. 6 is a view similar to FIGS. 4 and 5 showing a fourth embodiment of the coupling mechanism for the valve assembly and cannula base.

As mentioned above, the valve body and the cannula base are provided with coupling means so that the valve body may be attached to the cannula base before use and removed from the cannula base for disposal after use. FIGS. 1 and 2 described a screw coupling between the valve body and the cannula base. FIGS. 4–6 show other types of coupling means for coupling the valve body to the cannula base.

FIG. 4 shows a valve assembly 416 and a cannula base 414 which are provided with a bayonet coupling. In this embodiment, the valve body 460 of assembly 416 is provided with a cylindrical extension 465 having a pair of radially outward extending knobs 466a, 466b. Cylindrical extension 465 is also provided with an O-ring 161 which is substantially the same as the O-ring described above. Cannula base 414, according to this embodiment, is provided with a pair of bayonet grooves 464a, (464b not shown in the drawing) with knob receiving ends 481a, (481b not shown in the drawing) on the inner surface of its cylindrical passage 443. Those skilled in the art will appreciate that when the cylindrical extension 465 of valve body 460 is aligned so that the knobs 466 enter the grooves 464 of the cannula base 414, the two pieces may be pressed together. After the pieces are pressed snugly together, the pieces are rotated until the knobs 466 enter the knob receiving ends 481 of the bayonet grooves 464. The pieces are separated by twisting and pulling apart as understood in the art of bayonet coupling.

FIG. 5 shows a valve assembly 516 and a cannula base 514 which couple by means of a circumferential groove and a blade latch. In this embodiment the cylindrical extension 565 of the valve body 560 is provided with a circumferential groove 566. Cannula base 514 is provided with a sliding blade latch 564 which transects cylindrical passage 543. The blade latch has a circular opening 583 and a push button release handle 584 which is biased outward by a spring 585. When the blade latch is biased outward from the cannula base as shown, the circular opening 583 is axially offset from the cylindrical passage. In order to insert the valve body 560 into the cannula base 514, the push button 584 is depressed against spring 585 until the circular opening 583 is coaxial with cylindrical passage 543. After the cylindrical extension 565 of the valve body 560 is inserted into the cylindrical passage 543 of the cannula base 514, the push button 584 is released and spring 585 biases the blade latch to an offset position wherein the edge of opening 583 engages the groove 566. Releasing the two pieces is accomplished by pressing the push button and pulling them apart.

FIG. 6 shows a valve assembly 616 and a cannula base 614 which have a screw coupling different from that shown in FIGS. 1 and 2. Here, valve body 660 is provided with a distal sleeve 686 surrounding its cylindrical extension 665. Distal sleeve 686 has internal threads 666 which engage external threads 644 provided on the cannula base 614.

Coupling and uncoupling of these embodiments is similar to that described in FIGS. 1 and 2.

Figure 7:
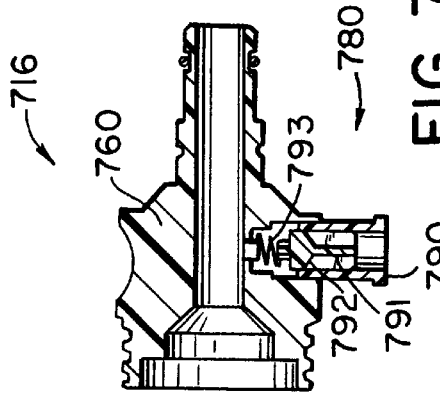
FIG. 7 is a longitudinal cross sectional view of another embodiment of the valve assembly for use with a cannula base coupling as shown in FIG. 5.

As mentioned above, the valve body may be provided with a side port. One example of a side port (manual stopcock) was described in FIG. 3. FIG. 7 shows another example of a side port 780 in a valve assembly 716. Here, side port 780 provides a female luer lock 790 and a preferably polymeric sliding valve 791 biased to a closed position against seat 792 by spring 793. Inserting a male luer, presses the valve 791 away from seat 792 to open a fluid passage. Removing the male luer allows valve 791 to be once again biased against seat 792 by spring 793. Additional detail regarding the valve is provided hereinafter with reference to FIGS. 12a–12c.

Figure 8:
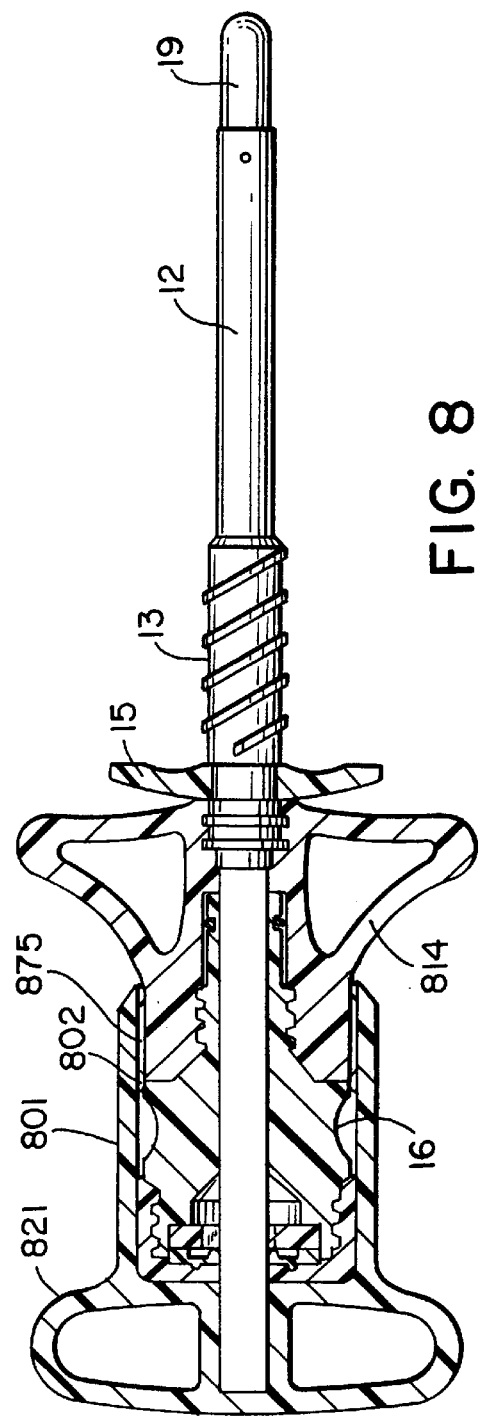
FIG. 8 is a view similar to FIGS. 1 and 3 showing a different embodiment of trocar handle.

As mentioned above with reference to FIGS. 1 and 2, the trocar handle 21 is preferably provided with anti-rotational means; namely a sleeve 201 with internal splines 202 which engage external splines 175 on the covering cap 164 of the valve body 160. In some embodiments, however, this anti-rotational scheme is not sufficient insofar as the valve body 160 is not prevented from rotation relative to the cannula base 14. FIG. 8 shows a different embodiment of the anti-rotational means where the trocar handle 821 is provided with an extended sleeve 801 having internal splines 802. In this embodiment, a cannula base 814 is provided with proximal external splines 875. As can be seen in FIG. 8, the extended sleeve 801 of the trocar handle 821 extends long enough to engage the splines 875 on the cannula base 814. This arrangement provides complete anti-rotational protection among the trocar handle, the valve body, and the cannula base. From the foregoing descriptions, it will be appreciated that when the trocar handle 821 and cannula base 814 are used in conjunction with a valve body having a side port such as those shown in FIGS. 3 and 7, a longitudinal cutout will be needed in the sleeve 801 to allow passage of the sleeve over the side port in the valve body.

Figure 9:
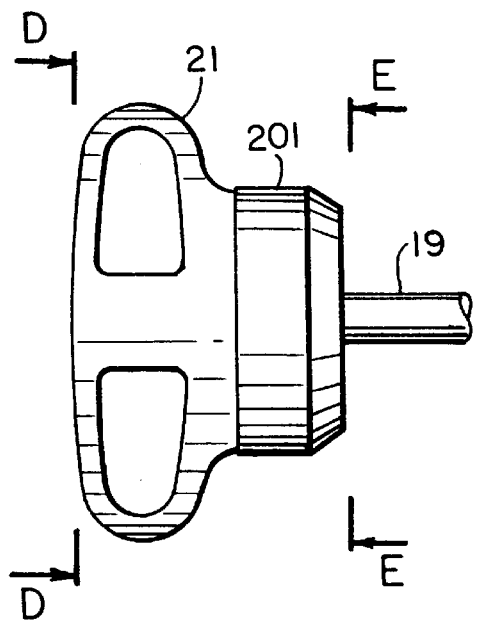
FIG. 9 is a side elevation view of the trocar handle shown in FIGS. 1–3.
Figure 9A:
FIGS. 9a–9c are side elevation views of different trocar tips.
Figure 9B:
Figure 10:
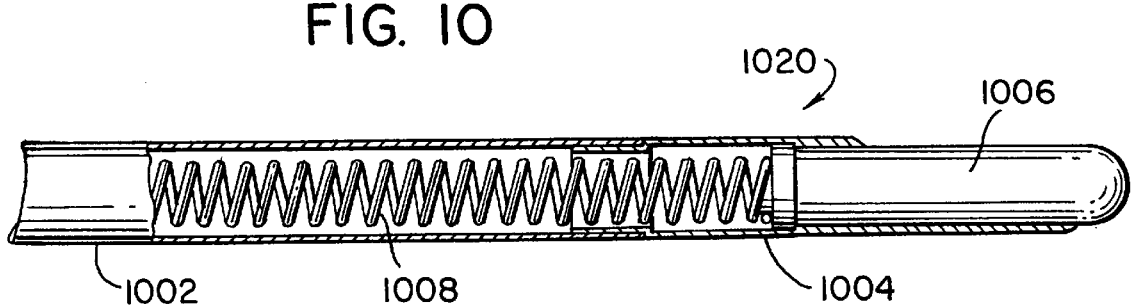
FIG. 10 is a side elevation view in partial longitudinal section of the safety trocar tip of FIG. 9b.
Figure 10A:
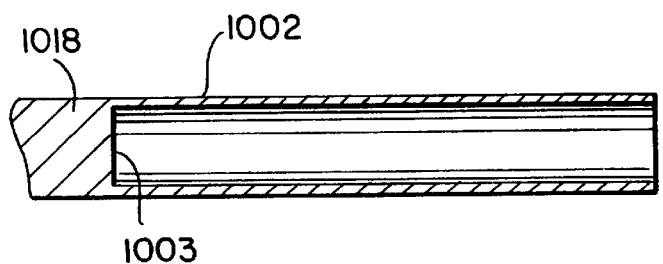
FIG. 10a is a longitudinal cross sectional view of recessed hollow for receiving the spring shown in FIG. 10.
Figure 10B:
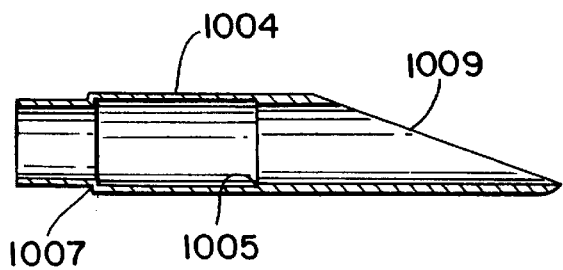
FIG. 10b is a longitudinal cross sectional view of the piercing point shown in FIG. 10.
Figure 10C:
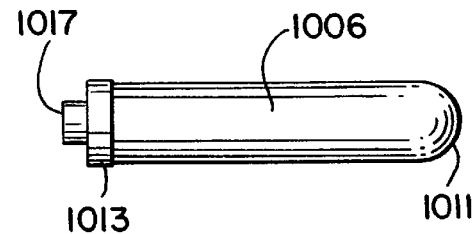
FIG. 10c is a side elevation view of the blunt spring biased safety tip shown in FIG. 10.

Several different types of trocars can be used with the trocar assembly of the invention. FIGS. 9 through 10c show details of different trocars and trocar handles.

Figure 9C:
Figure 9D:
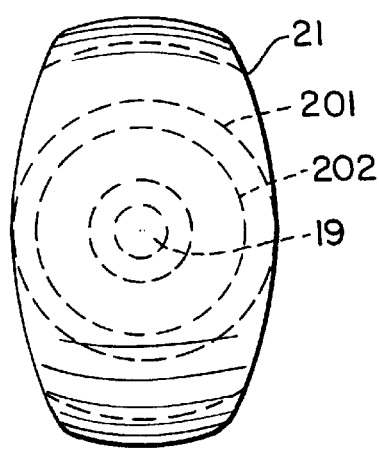
FIG. 9d is a top end view of the trocar handle taken in the direction D—D of FIG. 9.
Figure 9E:
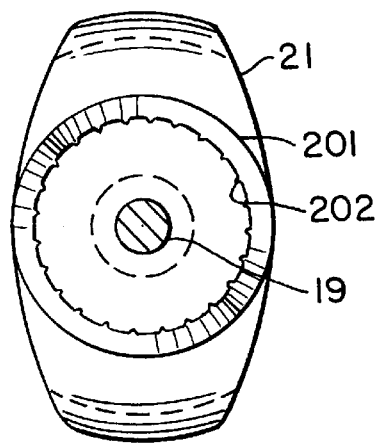
FIG. 9e is a bottom end view of the trocar handle taken in the direction E—E of FIG. 9.

Turning now to FIGS. 9—9e, a number of different tips 20, 920, 1020 may be provided on trocar 19 which is preferably insert molded into trocar handle 21. Trocar tip 20 is blunt and is preferred when a small incision such as might have been made by a scalpel blade or by a Veress needle is already available. Trocar tip 920 is a sharp pointed tip and is preferred when the trocar is used to incise the patient while inserting the trocar tube or cannula. When incising, however, it is important that the trocar not be inserted too deep, lest it pierce an internal organ. To guard against such an unintentional piercing, a safety tip 1020 may be provided on the end of a trocar for use with the trocar assembly of the invention. It should be appreciated by those skilled in the art will that any of the disclosed trocars may be provided with integral tips or with screw-in tips. In the screw-in tip arrangement, the distal end of the shaft of the trocar 19 would terminate with a male thread or a female threaded recess. Conversely, the proximal end of the tip portion would be provided with a female threaded recess or a male thread which would mate with the distal end of the shaft. With this arrangement, only the distal tip portion would need to be discarded after the tip was no longer usable.

Turning now to FIGS. 10, 10a, 10b, and 10c, a first embodiment of a safety trocar 1020 is provided. Safety trocar 1020 has a distal sleeve 1002 extending from shaft 1018 (which may extend to the handle or be provided with a screw mechanism for mating with another shaft) within which a spring 1008, a blunt tip 1006, and a piercing cylinder 1004 are mounted. The distal sleeve 1002 has a proximal end wall 1003 against which a proximal end of coil spring 1008 rests. The blunt tip 1006 has a rounded or otherwise blunt shaped distal end 1011 and a proximal spring engaging knob 1017. The blunt tip 1006 is also provided with a forward stop collar 1013 adjacent the spring engaging knob 1017. The piercing cylinder 1004 has a bias cut sharp distal end 1009, an interior forward stop shoulder 1005, and a reduced outer diameter sleeve mating portion 1007. Those skilled in the art will appreciate that the safety tip is assembled by placing the spring 1008 in the sleeve 1002, placing the blunt tip 1006 on top of the spring 1008, placing the piercing cylinder 1004 over the blunt tip and spring, and pressing the reduced diameter proximal end 1007 of the piercing cylinder into the sleeve 1002 against the force of spring 1008. The sleeve 1002 and piercing cylinder 1004 are preferably coupled by press fitting and mechanical staking. The distal end of the assembled safety trocar is shown in FIG. 10. Those skilled in the art will appreciate that when the trocar incises the patient, the blunt tip is pressed back against the spring until the sharp piercing cylinder is exposed to perform the incision. After the trocar pierces the outer cutaneous wall, the blunt tip is biased back to its original position as shown in FIG. 10 and offers a palpable resistance should the tip of the trocar contact an internal organ.

Figure 11:
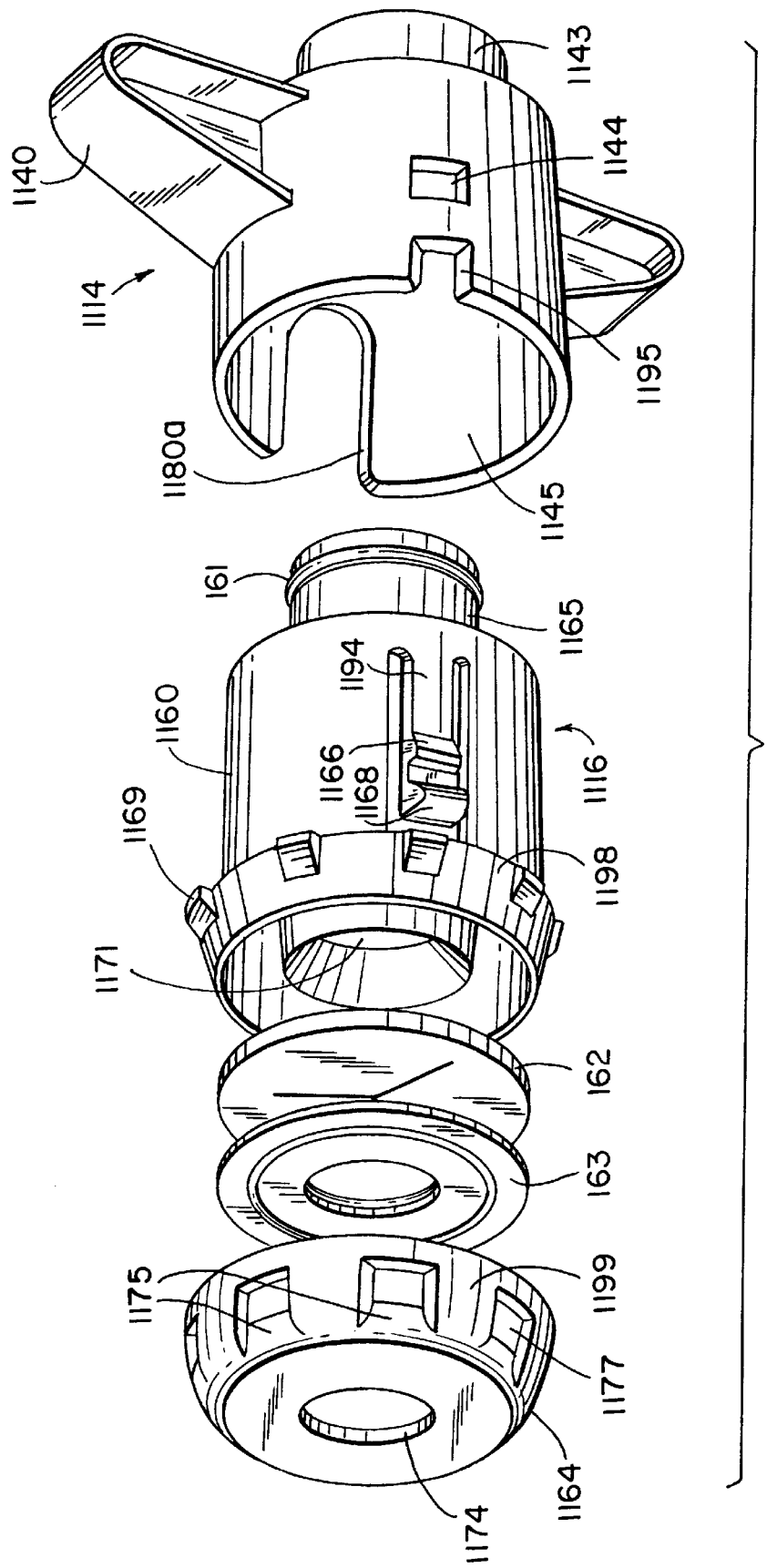
FIG. 11 is an exploded perspective view of yet another embodiment of the valve assembly and cannula base.

FIGS. 11, and 11a–11f show features of yet another embodiment of the invention. In FIGS. 11, 11b, 11e, and 11f, it can be seen that the valve assembly 1116 has a body 1160 which carries a distal O-ring 161. One side of the body 1160 is provided with a resilient tongue 1194 carrying a ramped tooth 1166 and a release button 1168 for releasably mating with the cannula base 1114. A side port 1180 is provided on the other side of the body 1160 as shown in FIG. 11b. Body 1160 has a cylindrical througbore 1171 which widens into a well 1173. The well 1173 receives the slit valve 162 and washer 163. A lip 1198 surrounding well 1173 is provided with two or more radially extending ramped mating teeth 1169 for mating with the valve cap 1164.

The valve cap 1164 has a central opening 1174 for receiving a trocar or other endoscopic instrument and two or more radial holes 1177 for engaging ramped teeth 1169. Holes 1172 are separated by ribs 1199. The valve assembly is assembled by placing slit valve 162 and universal washer 163 into the well 1173 or cap 1164 and snapping the valve cap 1164 over the lip 1198 of the valve body 1160 so that ramped teeth 1169 engage holes 1177. It will be appreciated that the teeth 1169 are ramped so that the cap 1164 may not be easily removed once the valve assembly is assembled.

The cannula base 1114 of the embodiment of FIGS. 11a–11f has a proximal mouth 1145 and a distal throat 1143. Mouth 1145 is provided with a longitudinal side cutout 1180a for receiving side port 1180 of the valve body 1160 and a similar though shorter side cutout 1195 for receiving release button 1168 of the valve body 1160. Distal of cutout 1195, a hole 1144 is provided for receiving and engaging ramped tooth 1166 of the valve assembly. The valve assembly is removably coupled to the cannula base by inserting the narrower distal portion 1165 of the valve assembly into the mouth 1145 of the cannula base 1114 so that the side port 1180 aligns with the cutout 1180a. Pressing the pieces together engages the O-ring 161 on the valve assembly 1116 with the throat 1143 of the cannula base 1114, and the tooth 1166 of the valve assembly with the hole 1144 in the cannula base 1114. It will be appreciated that the tooth 1166 is ramped to facilitate installation of the valve assembly in the cannula base and to prevent accidental removal. The release button 1168, when pressed, moves the tongue 1194 radially inward and thus removes the tooth 1166 from engagement with the hole 1144. It will therefore be appreciated that the pressing of the release button 1168 allows the valve assembly 1116 to be removed from the cannula base 1114 by pulling it out of the cannula base.

The trocar handle 1121 of FIGS. 11a–11f is provided with a sleeve 1101 having one or more internal splines 1102. When the trocar 1119 is inserted through opening 1174 in the cap of the valve assembly, splines 1101 fit snugly in the indentations 1175 between ribs 1199 and prevent rotation of the trocar handle relative to the valve assembly and cannula base. It will be appreciated that the splines 1102 of the handle 1121 and the teeth 1169 of the valve assembly are properly dimensioned so as not to interfere with each other when they are both in contact with the valve cap 1164.

A preferred safety tip trocar is shown in detail in FIGS. 11c and 11d. A hollow trocar cylinder 1118 having a sharp distal end 1109 is insert molded in handle 1121. A sliding blunt tip safety rod 1119 extends through the hollow trocar cylinder 1118 and beyond its distal end 1109. The proximal end of the rod 1119 is provided with a flange 1113a which limits its forward movement in the cylinder 1118, as well as a cylindrical hollow 1113b for receiving a spring 1108. Handle 1121 is provided with a cylindrical opening 1123 substantially coaxial with cylinder 1118 and rod 1119. A cylindrical cap 1103 is removably mounted by a threaded connection in cylindrical opening 1123 and the spring 1108 is interposed between the cap 1103 and the distal end of the hollow 1113b in the rod 1119. The spring 1108 biases the blunt tipped rod to its forward safety position as described above. The removable cap 1103 allows the removal of the spring 1108 and the rod 1119 for cleaning.

FIG. 11e is a longitudingal cross sectional view of the invention shown in FIG. 11 with a different type of trocar 1219 and trocar handle 1221. FIG. 11f is a cross section through the line F—F in FIG. 11e. Here the trocar is substantially the same as that described above with reference to FIG. 9c and the trocar handle 1221 is a solid piece into which trocar 1219 is insert molded. Trocar handle 1221 is in most ways the same as trocar handle 1121 described above, but for the spring holding cap 1103. FIGS. 11e and 11f show the relationship between cannula base 1114, valve assembly 1116, and trocar handle 1221. As shown, the cannula 1212 is provided with an integral proximal threaded collar 1213 as described above with reference to FIGS. 1 and 2.

Viewing FIGS. 11e and 11f, it can also be seen that the valve body 1160 comprises three substantially concentric cylinders 1160a, 1160b, 1160c. The innermost cylinder 1160a provides the through passage for the trocar and is coupled at its proximal end to a middle cylinder 1160b. The coupling of the innermost cylinder 1160 with the middle cylinder 1160b forms the proximal well 1173 in which slit valve 162 and universal washer 163 reside. The distal end of the middle cylinder 1160b extends into the relatively narrow distal end 1165 of the valve body which carries O-ring 161. Outermost cylinder 1160c extends from a point proximal of said O-ring to form the relatively larger diameter portion of the valve body which carries the teeth 1169, tongue 1194, and side port 1180. As will be seen below, the side port 1180 is actually carried by all three cylinders.

Figure 11G:
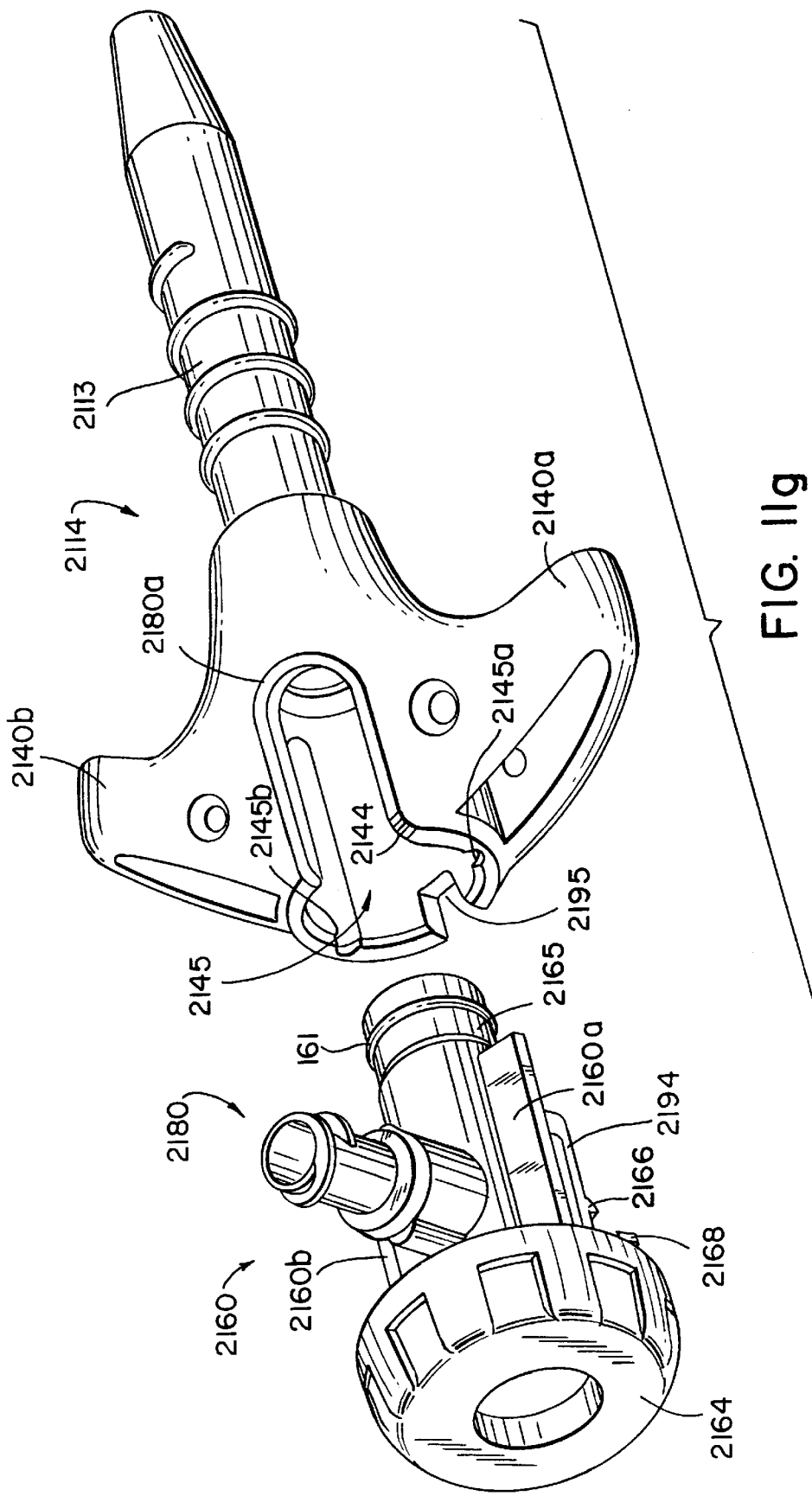
FIG. 11g is a view similar to FIG. 11, but of a slightly different embodiment of the invention.
Figure 11H:
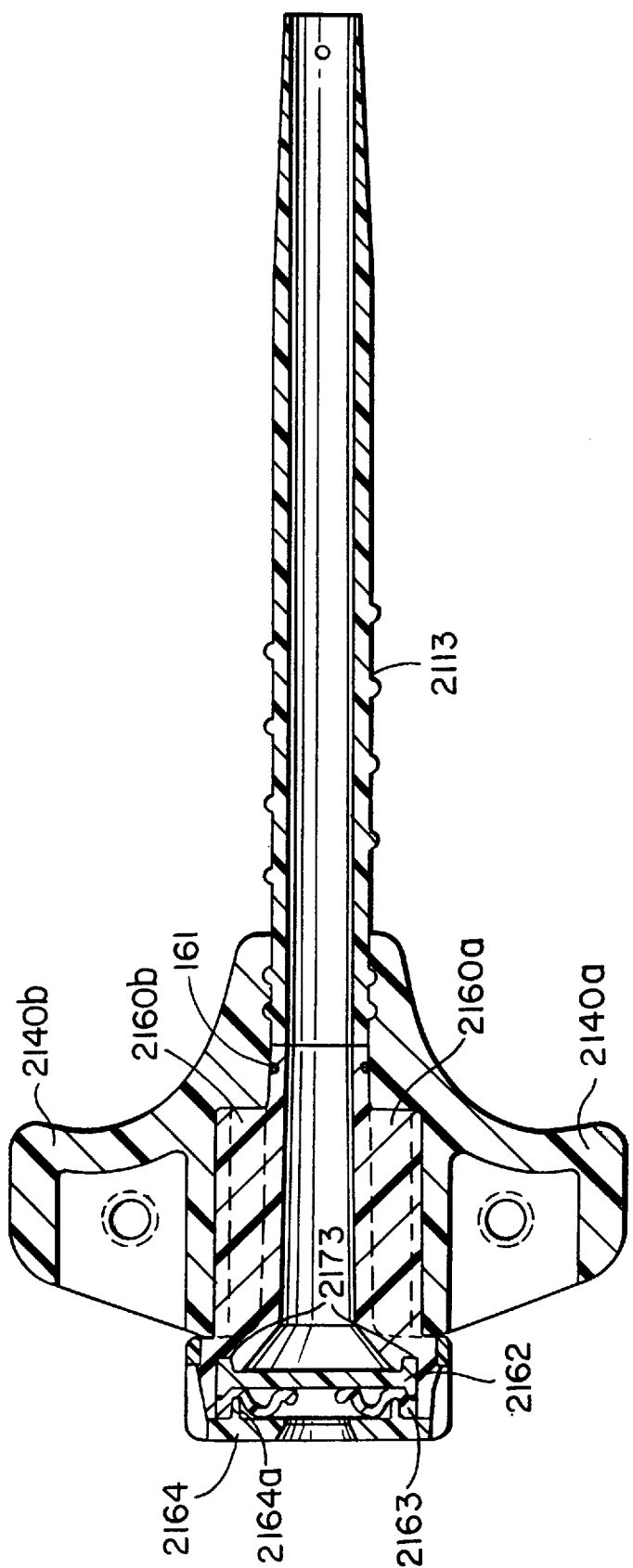
FIG. 11h is a view similar to FIG. 11e but of the embodiment of FIG. 11g.

FIGS. 11g and 11h show a slightly different embodiment of the valve body 2160, valves 2162, 2163, and cannula base 2114. In this embodiment, the valve body 2160 has a somewhat smaller overall diameter and is provided with lateral placement or retaining wings 2160a and 2160b. Valve body 2160 is also provided with a proximal annular groove 2173 for receiving the edge of a slit valve 2162 having a substantially I-shaped cross section. The valve body 2160 is otherwise substantially the same as previously described with reference to FIGS. 11a–11f, including the distal O-ring 161, the side port 2180, the resilient tongue 2194, ramped tooth 2166, and release button 2168. The valve body cap 2164 has an inner extending annular flange 2164a for engaging washer 2163 having a rippled cross section. The valve body cap 2164 is otherwise substantially the same as that which was previously described with reference to FIGS. 11a–11f.

The proximal mouth 2145 of the cannula base 2114 is of a somewhat smaller diameter than the cannula base described with reference to FIGS. 11a–11f, and it is provided with adjacent slots 2145a, 2145b for receiving the wings 2160a, 2160b of the valve body 2160. In this manner, the valve assembly 2160 is located and centered in the cannula base 2114, and-the valve assembly 2160 cannot slide out of the side opening 2180a. The external flanges 2140a, 2140b in this embodiment of the cannula base are shaped differently for easier gripping. The side cutouts 2180a, 2144 and 2195 for receiving the side port 2180, ramped tooth 2166, and release button 2168 of the valve body are substantially the same as in the previously described embodiment FIGS. 11a–11f.

Figure 12B:
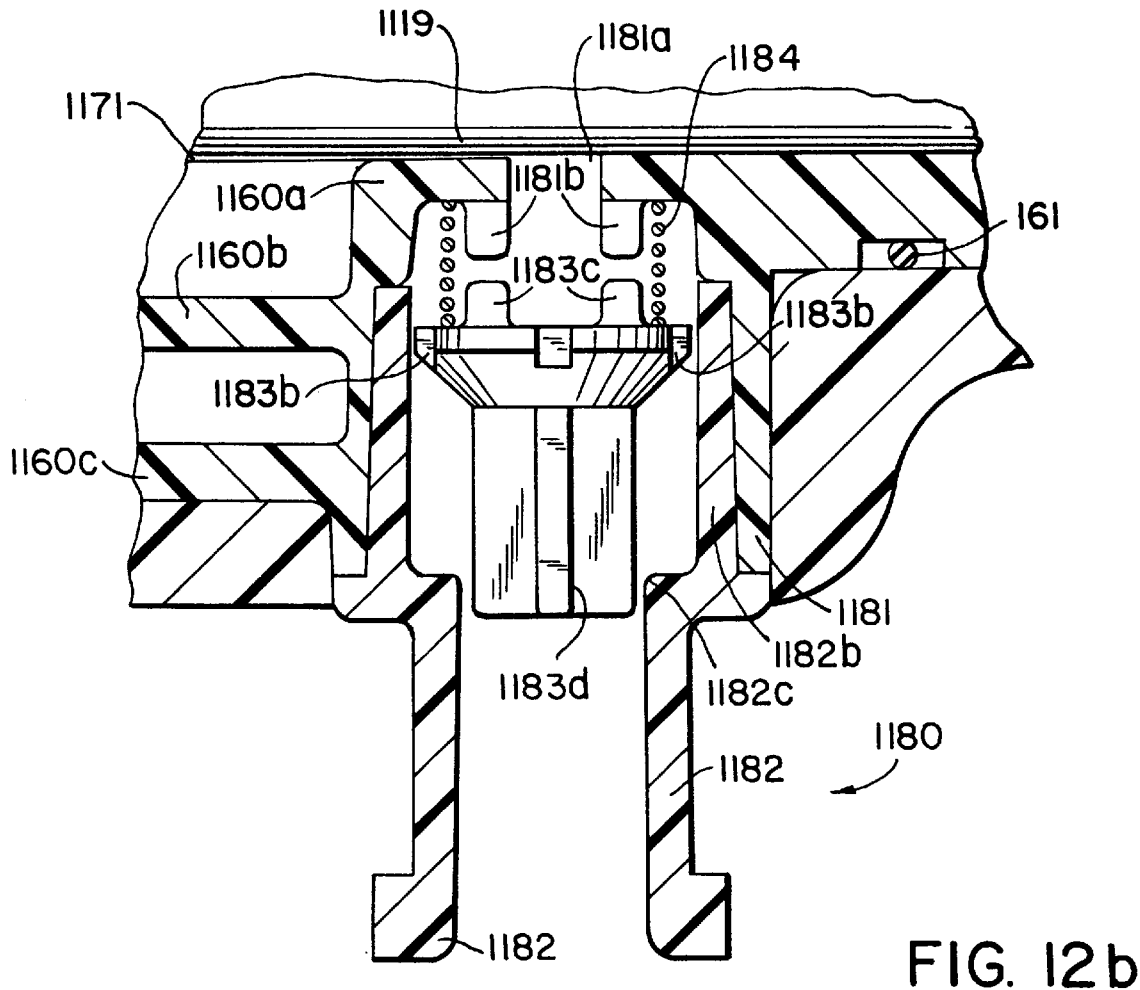
Figure 12C:
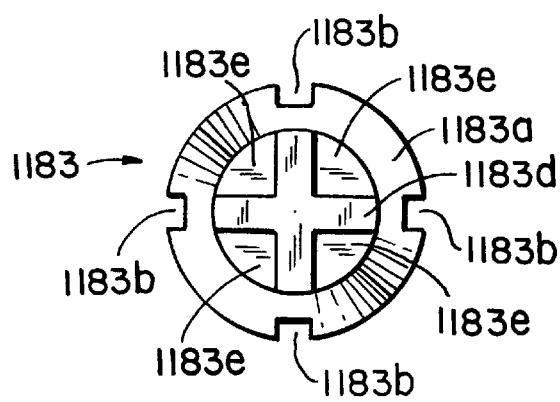
FIG. 12c is a end view of the plunger of the preferred valve means of FIGS. 12a and 12b.

FIGS. 12a–12c show details of the side port 1180 of the preferred embodiment of the invention. Referring in particular to FIG. 12a, the side port 1180 is formed by a radially extending opening 1181 through the valve body 1160. Opening 1181 is substantially cylindrical with a central bore 1181a communicating with the throughbore 1171 of the valve body 1160. One end of a spring 1184 is held substantially coaxial with bore 1181a by spring stop 1181b. The other end of spring 1184 carries a valve plunger 1183 having a frustrum 1183a with vents 1183b, spring stop 1183c and a plunger actuator 1183d. A female luer 1182 having a threaded luer lock 1182a and a reduced diameter extending portion 1182b and a shoulder 1182c is inserted into opening 1181 and locked and/or sealed by an adhesive, sonic welding, snap lock, or other acceptable means. As seen in FIG. 12a, spring 1184 biases the frustrum 1183a of plunger 1183 against the shoulder 1182c of luer 1182 preventing fluid passage into or out of the luer 1182. When a male luer (not shown) is coupled to the female luer 1182, the plunger 1183 is pressed inward against spring 1184 as shown in FIG. 12b.

Referring now to FIGS. 12b and 12c, it will be appreciated that the plunger actuator 1183d is a cross (+) shaped rod having four surrounding fluid passages 1183e. Moreover, an end portion of frustrum 1183a is provided with circumferential vents 1183b. When the plunger 1183 is pressed in away from shoulder 1182c, fluid is permitted to flow into and out of luer 1182 as a path is created from bore 1181a through spring 1184, vents 1183b and passages 1183e to luer 1182.

There have been described and illustrated herein several embodiments of a reusable trocar assembly having a disposable valve structure. While particular embodiments of the invention have been described, it is not intended that the invention be limited thereto, as it is intended that the invention be as broad in scope as the art will allow and that the specification be read likewise. Thus, while particular fabrication materials have been disclosed, it will be appreciated that other materials could be utilized. Also, while certain specific trocar tips have been shown, it will be recognized that other types of trocar tips could be used with similar results obtained. Moreover, while particular configurations have been disclosed in reference to the trocar handle and cannula base, it will be appreciated that other configurations could be used as well. Furthermore, while the disposable valve assembly has been disclosed as having a slit valve or flapper valve and a universal washer, it will be understood that different valve means housed in the valve body can achieve the same or similar function as disclosed herein. Finally, several coupling means have been disclosed for removably coupling the valve assembly to the cannula base. It will be understood that these means are exemplary and that other coupling means could achieve substantially the same results in substantially the same manner. It will therefore be appreciated by those skilled in the art that yet other modifications could be made to the provided invention without deviating from its spirit and scope as so claimed.

We claim:

1. A valve assembly for use in a trocar assembly where the trocar assembly includes a cannula assembly having a first coupling means and a hollow cannula, and a trocar having a proximal handle and an elongate element with the elongate element extending through the valve assembly and hollow cannula, said valve assembly comprising:
   a) a valve body defining a fluid passage dimensioned to permit the trocar to extend therethrough;
   b) an automatic valve means in fluid communication with said fluid passage, said automatic valve means for permitting the trocar to be inserted through said automatic valve means and for automatically closing said fluid passage when said trocar is removed from said automatic valve means; and
   c) a fluid seal means, wherein
      said valve body has a distal portion and said fluid seal means surrounds said distal portion of said valve body.
      said valve body includes valve body coupling means for removably coupling said valve assembly with the first coupling means of the cannula assembly to effect a fluid coupling of said fluid passage with said cannula, and
      said valve body coupling means comprises one of a threaded portion, a bayonet locking mechanism, and a latch mechanism on said valve body which mates with the first coupling means of the cannula assembly.

2. A valve assembly according to claim 1, wherein:
said distal portion of said valve body has a circumferential groove, and said fluid seal means comprises an O-ring sitting in said circumferential groove.

3. A valve assembly according to claim 2, wherein:
said valve body includes a well for receiving said automatic valve means, and said valve assembly further includes a valve cap for covering said well, said valve cap having a central opening dimensioned to receive the trocar.

4. A valve assembly according to claim 3, wherein:
said valve body and said valve cap have second and third coupling means for coupling with each other and holding said automatic valve means in place.

5. A valve assembly according to claim 4, wherein:
said second coupling means comprises a plurality of ramped teeth, and
said third coupling means comprises a plurality of radial openings in said valve cap, wherein said plurality of ramped teeth mate with and fit inside said plurality of radial openings.

6. A valve assembly according to claim 1, wherein:
said valve body coupling means is on an external surface of said valve body, and comprises one of an external thread, a bayonet groove, a bayonet knob, and a circumferential groove on said valve body.

7. A valve assembly according to claim 1, wherein:
said valve body coupling means is on an internal surface of said valve body, and comprises one of an internal thread, a bayonet groove, and a bayonet knob.

8. A valve assembly according to claim 1, wherein:
said latch mechanism comprises a resilient tongue having a protrusion extending outward from said resilient tongue.

9. A valve assembly according to claim 8, wherein:
said resilient tongue comprises a cantilevered cut-out in a wall of said valve body.

10. A valve assembly according to claim 9, wherein:
said resilient tongue further includes a release mechanism extending outward from said resilient tongue, wherein upon squeezing said release mechanism, said protrusion disengages from the first coupling means of the cannula assembly.

11. A valve assembly according to claim 1, wherein:
said automatic valve means comprises a flapper valve and an elastic washer, said elastic washer having an annular opening providing a first contact surface and a circumferential portion which provides a second contact surface, said elastic washer being mounted in said fluid passage within said valve body.

12. A valve assembly according to claim 11, wherein:
said flapper valve comprises a resilient arm member and a contact member coupled to said resilient arm member, wherein, in a first closed position, said resilient arm member is bent to provide a force which pushes said contact member into contact with said second contact surface of said elastic washer.

13. A valve assembly according to claim 12, wherein:
said resilient arm member is made of silicone rubber, and
said contact member is made of a polymeric material.

14. A valve assembly according to claim 11, wherein:
said flapper valve comprises a spring loaded arm member coupled to a circumferential contact member, said circumferential contact member being in contact with said second contact portion of said elastic washer when said spring loaded arm member is in a first spring loaded position.

15. A valve assembly according to claim 14, wherein:
said flapper valve includes a fixed pin, and
said spring loaded arm member comprises a spring and a first arm coupled to said spring, at least one of said spring and said first arm extending and rotating around said fixed pin.

16. A valve assembly according to claim 15, wherein:
said spring loaded arm member further comprises a second arm which includes said circumferential contact member, and
one of said first arm and said second arm has a rounded protrusion extending therefrom towards the other of said first arm and said second arm, and the other of said first arm and second arm includes a socket for receiving said rounded protrusion.

17. A valve assembly according to claim 16, wherein:
said protrusion and said socket are shaped to cause said first arm to be coupled to said second arm, but to allow some movement of said first arm relative to said second arm so that said circumferential contact member properly seats against said second contact portion of said elastic washer.

18. A valve assembly according to claim 15, wherein:

said valve body includes a side insufflation port in fluid contact with said fluid passage, and said spring has a first end anchored in said insufflation port and a second end anchored in said first arm.

19. A valve assembly according to claim 14, wherein:

said arm member has a curved end portion which curves away from said elastic washer and which protects said arm member from contact with an instrument inserted through said disposable valve assembly except along a top surface of said arm member when said spring loaded arm member is in a second opened position where said circumferential contact member is not in contact with said second contact portion of said elastic washer.

20. A valve assembly according to claim 1, wherein:

said valve body includes a side port means for coupling with a fluid conduit, said side port in fluid communication with said fluid passage of said valve assembly.

21. A trocar assembly according to claim 20, wherein:

said side port comprises a luer means with a spring biased valve member.

22. A valve assembly for use in a trocar assembly where the trocar assembly includes a cannula assembly having a first coupling means and a hollow cannula, and a trocar having a proximal handle And an elongate element with the elongate element extending through the valve assembly and hollow cannula, said valve assembly comprising:

a) a valve body defining a fluid passage dimensioned to permit the trocar to extend therethrough; and b) an automatic valve means in fluid communication with said fluid passage, said automatic valve means for permitting the trocar to be inserted through said automatic valve means and for automatically closing said fluid passage when said trocar is removed from said automatic valve means, wherein said valve body includes valve body coupling means for removably coupling said valve assembly with the first coupling means of the cannula assembly to effect a fluid coupling of said fluid passage with said cannula.

said valve body coupling means comprises one of a threaded portion, a bayonet locking mechanism, and a latch mechanism on said valve body which mates with the first coupling means of the cannula assembly, and said automatic valve means comprises a slit valve having a plurality of trocar engaging protrusions which protrude axially from and which are spaced around said slit valve.

23. A valve assembly according to claim 22, wherein:

said slit valve is a tricuspid valve, and said plurality of trocar engaging protrusions comprises at least three trocar engaging protrusions.

24. A valve assembly for use with a medical instrument and a tubular assembly having a first coupling means, said valve assembly comprising:

a) a valve body defining a fluid passage;

b) an automatic valve means in fluid communication with said fluid passage, said automatic valve means for permitting the medical instrument to be inserted through said automatic valve means and for automatically closing said fluid passage when the medical instrument is removed from said automatic valve means; and c) a fluid seal means, wherein said valve body has a distal portion and said fluid seal means surrounds said distal portion of said valve body, said valve body includes valve body coupling means for removably coupling said valve assembly with the first coupling means of the tubular assembly to effect a fluid coupling of said fluid passage with said tubular assembly, and said valve body coupling means comprises one of a threaded portion, a bayonet locking mechanism, and a latch mechanism on said valve body which mates with the first coupling means of the tubular assembly.

* * * * *